United States Patent
Edgell et al.

(10) Patent No.: US 11,814,658 B2
(45) Date of Patent: *Nov. 14, 2023

(54) LIPID-ENCAPSULATED DUAL-CLEAVING ENDONUCLEASE FOR DNA AND GENE EDITING

(71) Applicant: SPECIFIC BIOLOGICS INC., Toronto (CA)

(72) Inventors: David R. Edgell, London (CA); Thomas A. McMurrough, London (CA); Brent E. Stead, Toronto (CA); Odisho K. Israel, Toronto (CA)

(73) Assignee: Specific Biologics Inc., Toronto (CA)

( * ) Notice: Subject to any disclaimer, the term of this patent is extended or adjusted under 35 U.S.C. 154(b) by 0 days.

This patent is subject to a terminal disclaimer.

(21) Appl. No.: 18/055,713

(22) Filed: Nov. 15, 2022

(65) Prior Publication Data

US 2023/0203464 A1 Jun. 29, 2023

Related U.S. Application Data

(63) Continuation of application No. 17/514,585, filed on Oct. 29, 2021, which is a continuation of application No. PCT/IB2020/054229, filed on May 4, 2020.

(60) Provisional application No. 62/842,586, filed on May 3, 2019, provisional application No. 63/019,423, filed on May 3, 2020.

(51) Int. Cl.
| | |
|---|---|
| *C12N 9/22* | (2006.01) |
| *A61K 31/7088* | (2006.01) |
| *A61K 38/46* | (2006.01) |
| *C12N 15/01* | (2006.01) |
| *C12N 15/90* | (2006.01) |
| *C12N 15/11* | (2006.01) |

(52) U.S. Cl.
CPC ............ *C12N 9/22* (2013.01); *A61K 31/7088* (2013.01); *A61K 38/465* (2013.01); *C12N 15/11* (2013.01); *C12N 15/907* (2013.01); *C12N 2310/20* (2017.05); *C12N 2800/80* (2013.01)

(58) Field of Classification Search
CPC ........ C12N 9/22; C12N 15/11; C12N 15/907; C12N 2310/20; C12N 2800/80; A61K 31/7088; A61K 38/465
See application file for complete search history.

(56) References Cited

U.S. PATENT DOCUMENTS

| | | | |
|---|---|---|---|
| 8,865,406 B2 | 10/2014 | Zhang et al. | |
| 11,491,207 B2 * | 11/2022 | Khalili | .................. C12N 15/00 |
| 2022/0195404 A1 * | 6/2022 | Edgell | ................ A61K 31/7088 |
| 2023/0016280 A1 * | 1/2023 | Edgell | ................ A61K 31/7088 |

FOREIGN PATENT DOCUMENTS

| | | | | |
|---|---|---|---|---|
| WO | WO 2013/068845 A2 * | 5/2013 | ............... | C12N 9/22 |
| WO | 2014093622 A2 | 6/2014 | | |
| WO | 2014121222 A1 | 8/2014 | | |
| WO | 2018237369 A2 | 12/2018 | | |
| WO | 2019060469 A2 | 3/2019 | | |

OTHER PUBLICATIONS

Chang et al., Integrating Combinatorial Lipid Nanoparticle and Chemically Modified Protein for Intracellular Delivery and Genome Editing. Acc. Chem. Res., 2019, vol. 52: 665-675 (Year: 2019).*
Wang et al., Delivery of the Cas9 or TevCas9 System into Phaeodactylum tricornutum viaConjugation of Plasmids from a Bacterial Donor. Bio-Protocol, 2018, vol. 8(16), e2974, pp. 1-14. (Year: 2018).*
Wishart et al., A single mutation converts a novel phosphotyrosine binding domain into a dual-specificity phosphatase. J. Biol. Chem., 1995, vol. 270(45): 26782-26785. (Year: 1995).*
Witkowski et al., Conversion of b-ketoacyl synthase to a Malonyl Decarboxylase by replacement of the active cysteine with glutamine. Biochemistry, 1999, vol. 38: 11643-11650. (Year: 1999).*
Wolfs et al., Biasing genome-editing events toward precise length deletions with an RNA-guided TevCas9 dual nuclease. PNAS., 2016, vol. 113(52): 14988-14993. (Year: 2016).*
Guha et al. (Nov. 29, 2017) "Applications of Alternative Nucleases in the Age of CRISPR/Cas9", International Journal of Molecular Sciences, 18(12):2565 (13 pages).
International Preliminary Report on Patentability for Application No. PCT/IB2020/054229, dated Nov. 9, 2021, 8 pages.
International Search Report and Written Opinion for Application No. PCT/IB2020/054229, dated Jul. 29, 2020, 16 pages.

* cited by examiner

Primary Examiner — Ganapathirama Raghu
(74) Attorney, Agent, or Firm — Mintz, Levin, Cohn, Ferris, Glovsky and Popeo, P.C.

(57) ABSTRACT

Methods to edit genes by administering a chimeric nuclease to a cell or organism without the use of a viral vector.

18 Claims, 7 Drawing Sheets

Specification includes a Sequence Listing.

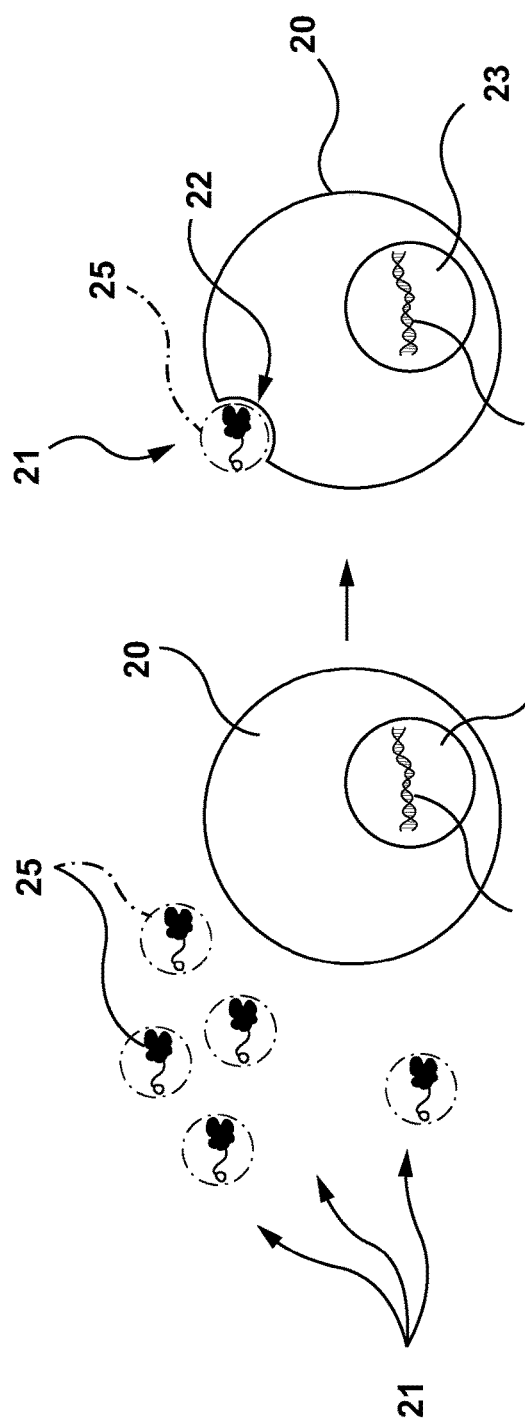
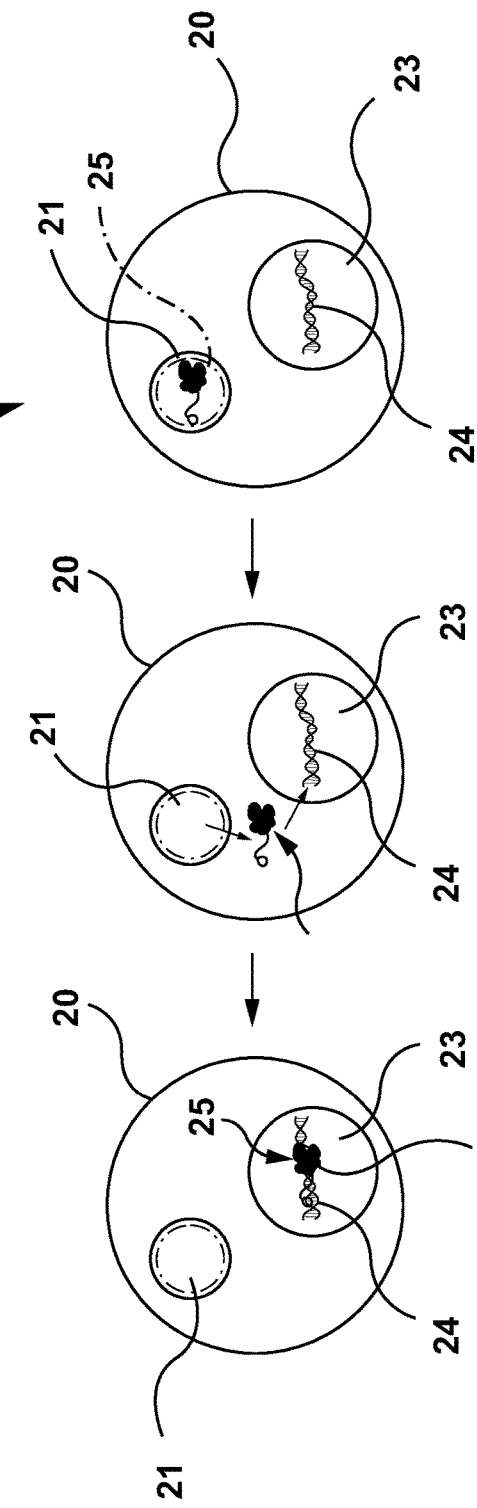

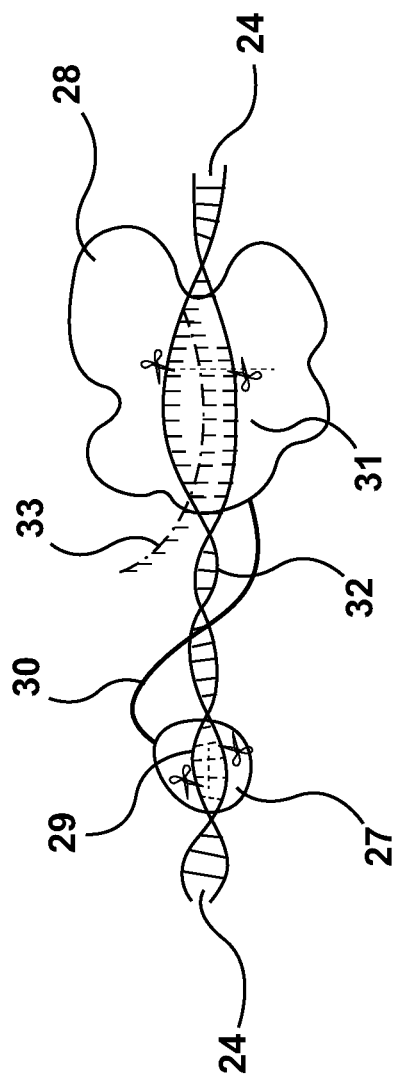
FIG. 3A
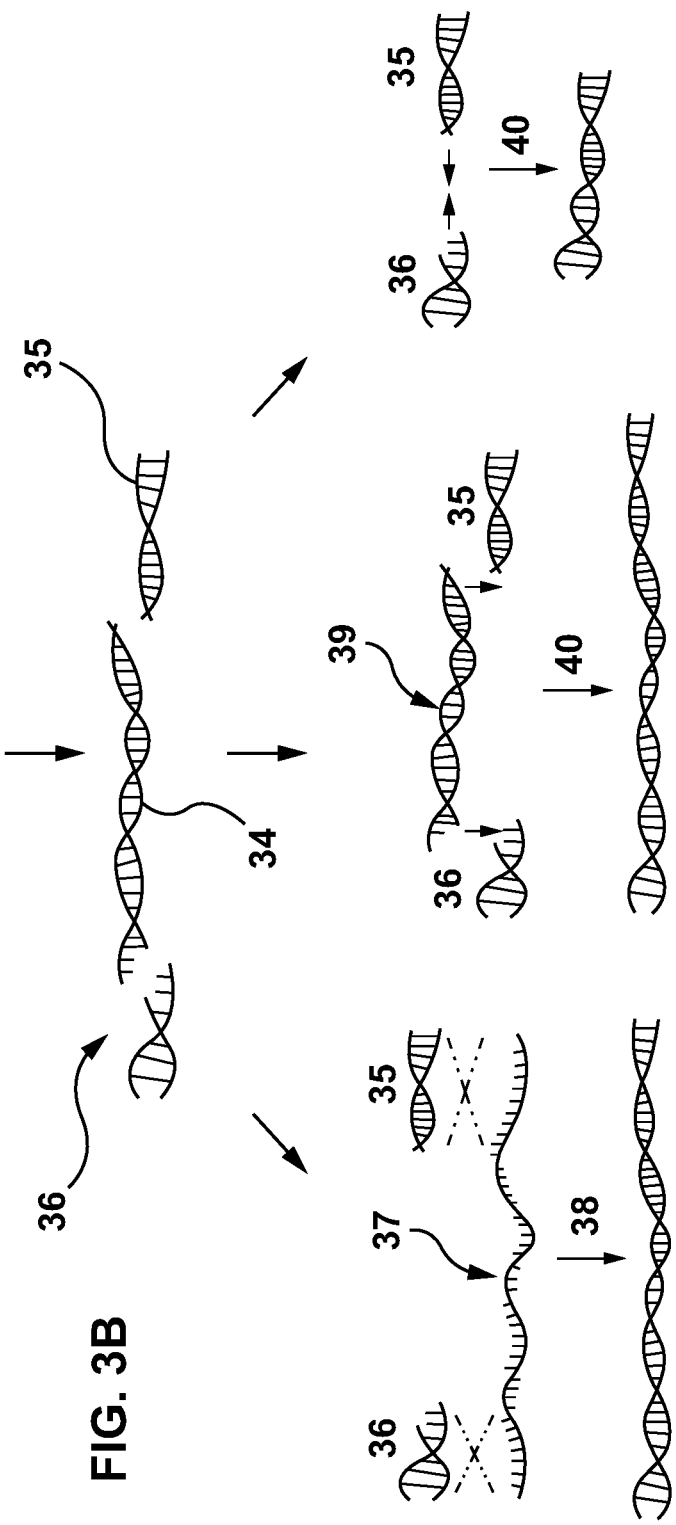
FIG. 3B
FIG. 3C
FIG. 3D
FIG. 3E

LIPID-ENCAPSULATED DUAL-CLEAVING ENDONUCLEASE FOR DNA AND GENE EDITING

CROSS-REFERENCE

This application is a continuation of U.S. application Ser. No. 17/514,585, filed Oct. 29, 2021, which is a continuation of International application number PCT/M2020/054229, filed May 4, 2020, which claims benefit of U.S. provisional application No. 62/842,586, filed May 3, 2019, and 63/019,423, filed May 3, 2020, each of which is herein incorporated by reference in its entirety.

SEQUENCE LISTING

The instant application contains a Sequence Listing which has been submitted in ST.26 XML format via patent Center and is hereby incorporated by reference in its entirety. Said ST.26 XML copy, created on Nov. 15, 2022, is named 61414-701-301-SL.xml and is 48,195 bytes in size.

BACKGROUND OF THE INVENTION

There are an estimated 5,000-10,000 monogenic diseases, defined as inherited conditions arising from mutations on a single gene. These diseases often manifest during childhood and lead to a variety of conditions and sometimes premature death. It has been estimated that together they will affect about 6% of people at some point in their lives. Diagnosis and treatment for these diseases remain largely insufficient, and the care is primarily palliative, focusing on disease management without addressing the underlying genetic defects. There are also many more diseases in which a mutation to a gene contributes to the pathogenesis of the disease.

Gene editing is a gene therapy approach that relies on designer nucleases to recognize and cut specific DNA sequences, and subsequently exploits innate cellular DNA repair pathways, namely nonhomologous end joining (NHEJ) and homology directed repair (HDR), to introduce targeted modifications in the genome. Four nuclease families have been used in this context: meganucleases, zinc-finger nucleases (ZFNs), transcription activator-like effector nucleases (TALENS), and clustered regulatory interspaced short palindromic repeats associated RNA-guided Cas9 (CRISPR-Cas9) nucleases. These can be designed to precisely introduce a double stranded break at the target locus of interest. Gene editing opens up the possibility of permanently modifying a genomic sequence of interest by enabling targeted disruption, insertion, excision, and correction in both ex vivo and in vivo settings. While these advances are expected to revolutionize the field at large, current gene-editing approaches are limited by efficacy of modification, safety concerns related to the specificity of nucleases, and delivery of gene-editing tools to target cell types.

A component of the type II CRISPR system that constitutes the innate immune system of bacteria, the Cas9 (CRISPR-associated) protein has caused a paradigm shift in the field of genome editing due to its ease-of-use. Programming Cas9 to cleave a desired sequence is a simple matter of changing the sequence of the Cas9-associated guide RNA to be complementary to the target site. The ease of programming Cas9 targeting contrasts with the more intensive protein engineering that is required for other reagents (zinc finger nucleases (ZFNs), meganucleases, transcription activator-like effector nucleases (TALENs)). Cas9, along with proteins from type III CRISPR systems have been used for a myriad of genome-editing applications in a diverse range of organisms and are now entering the realm of therapeutic applications in humans.

Cystic fibrosis (CF) is an autosomal-recessive disease resulting from mutations in the CFTR gene, which encodes an epithelial anion channel. The CFTR protein, cystic fibrosis transmembrane conductance regulator, is found across a wide range of organs including pancreas, kidney, liver, lungs, gastrointestinal tracts, and reproductive tracts, making CF a multiorgan disease. Mutations in CFTR lead to suboptimal ion transport and fluid retention, causing the prominent clinical manifestations of abnormal thickening of the mucus in lungs and pancreatic insufficiency. In the lung, dysfunctional CFTR hinders mucociliary clearance, rendering the organ susceptible to bacterial infections and inflammation, ultimately leading to airway occlusion, respiratory failure, and premature death. CF remains the most common and lethal genetic disease among the Caucasian population with 70,000-100,000 sufferers estimated worldwide, highlighting a real need for the development of better treatments.

One major challenge to the development of a therapeutic strategy for CF is the wide diversity of mutation types. Delta F508 (deletion of phenylalanine at codon 508) mutation, with a prevalence of >80% in CF patients, is by far the most common, but more than 1,990 deleterious CFTR-mutations have been described. These mutations cause premature stop codons, aberrant splicing, incorrect protein folding or trafficking to the cell surface, and dysfunctional CFTRs with limited channel-opening capacity. Pharmacological interventions have been targeted to several of these processes and while drug administration is therapeutic in some gating mutation types, the commonly occurring delta F508 still requires a more effective treatment. Pharmaceutical advancement in the care of CF, however, does not address mutations resulting from aberrant splicing or premature stop codons; it is in these instances gene editing could prove most beneficial.

Similarly, in the Western population, approximately 15% of patients with non-small cell lung cancer (NSCLC) harbor an activating mutation in their tumor in the EGF receptor (EGFR) gene.

Existing gene editing technologies, such as CRISPR-Cas9 (and Cas9 fusions), meganucleases, zinc finger proteins, type IIS restriction endonucleases (FokI and FokI fusions) and TALENS are limited in the ability to introduce gene deletions of a specific length or to accurately repair a target gene in a sufficient number of cells to be meaningful as a therapeutic agent for many genetic diseases. Moreover, for highly programmable RNA-guided nucleases, such as the monomeric Cas9, studies suggest that the specificity for predictably binding, cleaving and repairing only their target sites is limited, raising concerns over potential deleterious changes to a cell's genomic DNA that may inadvertently cause a secondary disease in a patient. Last, most nucleases are delivered in viral vectors. Viral vectors have the potential for: existing immunity in many populations; immunogenicity after treatment; and genotoxicity. No non-viral delivery method exists today to safely deliver the nuclease to target cells and allow for controlled dosing of the nuclease in vivo.

There is an unmet need for improvements to said existing gene editing technologies to address the above concerns to make gene editing technologies more efficient and effective.

BRIEF DESCRIPTION OF THE DRAWINGS

FIG. 2A to 2E is a diagram of the mechanism by which lipid-encapsulated TevCas9 is internalized into a cell and nucleus to reach its target DNA. As illustrated in FIG. 2A, a cell 20 or cells 20 are exposed to the novel lipid-encapsulated nuclease particles 21 containing the TevCas9 25 either by in vivo or ex vivo administration. As shown in FIG. 2B, the lipid-encapsulated nuclease particle 21 is endocytosed into the cell 20. The endosome 22 goes through a maturation process in the cytosol and is targeted for degradation (FIG. 2C). On certain occasions, the TevCas9 25 can escape the endosome 22 and enter the cytosol (FIG. 2D). In eukaryotic organisms, the nuclease (TevCas9) 25 is targeted to the nucleus 23 of the cell 20 through one or more nuclear-localization sequences ("NLS"). As depicted in FIG. 2E, through its nuclear localization sequence, TevCas9 25 can enter the nucleus 23 and when in the nucleus 23, the TevCas9 nuclease 25 binds to and cleaves 26 the target genomic DNA 24 sequence.

FIG. 3A to 3E is a diagram of the mechanisms by which lipid-encapsulated TevCas9 modifies target DNA. The I-TevI domain 27 targets the I-TevI Target Sequence 29. The linker domain 30 joins the I-TevI domain 27 with the Cas9 domain 28 which targets the Cas9 Target Sequence 31. The gene mutation 32 is surrounded by or in close proximity to the I-TevI Target Sequence 29 and the Cas9 Target Sequence 31. As shown in FIG. 3B, the TevCas9 25 cleaves the target sequence leaving a deletion product 34 of a predictable size with non-complementary DNA ends 35, 36. FIG. 3C illustrates that in the presence of single-stranded donor DNA with homology arms 37, the cell 20 can insert the donor DNA 37 sequence near the cut sites through the homology-directed repair (HDR) pathway 38. FIG. 3D illustrates that in the presence of donor DNA 39 with compatible DNA ends to those cleaved by TevCas9 25, the cell 20 can insert the donor DNA sequence 39 between the cut sites through directed-ligation using the non-homologous end joining (NHEJ) pathway 40. In the absence of donor DNA, the cell 20 can join the DNA ends through the NHEJ pathway 40 (FIG. 3E).

BRIEF SUMMARY OF THE INVENTION

Figure 1:
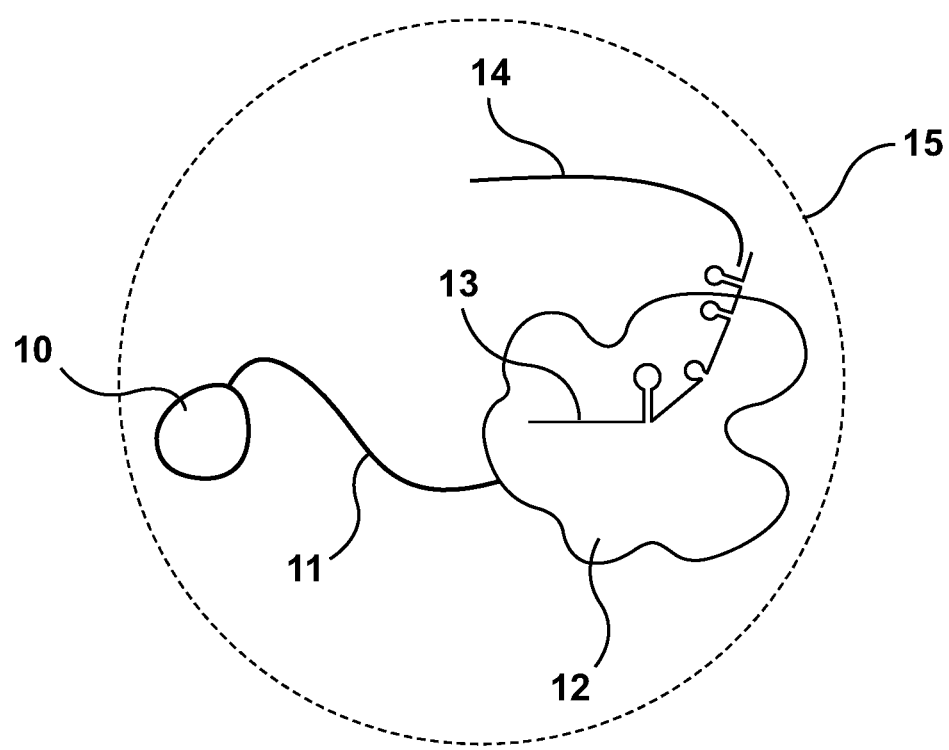
FIG. 1 is a schematic representation of the lipid-encapsulated dual-cleaving nuclease (TevCas9) after it has been prepared [Components are not to scale]. The I-TevI Domain 10 is joined to the RNA-guided Nuclease (Cas9) Domain 12 via a Linker Domain 11. In the preferred embodiment, the formed particles also contain Guide RNA 13 and Donor DNA 14. The aforementioned nuclease is contained in a Lipid Particle 15 which has been shaped into a sphere using an extrusion process.
Figure 4A:
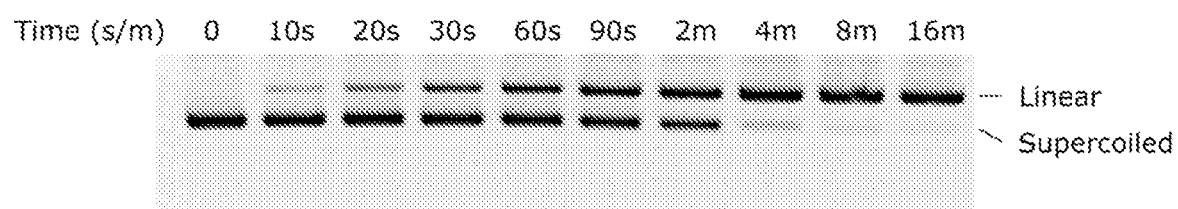
FIG. 4A evidences that TevCas9, targeted to the CFTR gene using guide in SEQ ID 15, cleaves CFTR DNA substrate in vitro.
Figure 4B:
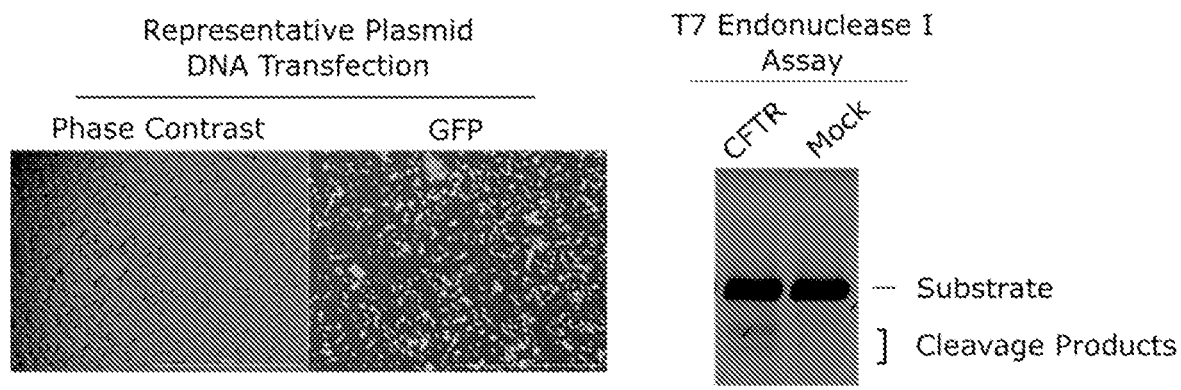
FIG. 4B are cells transfected with a plasmid DNA version of TevCas9 fused to a cleavable GFP tag imaged using phase contrast and GFP imaging on a Cytation5 (Biotek Instruments Inc, VT, USA) after 48 hours treatment. Genomic DNA is extracted from harvested cells and editing at the CFTR gene is detected by PCR amplification and a T7 Endonuclease I cleavage assay.
Figure 5:
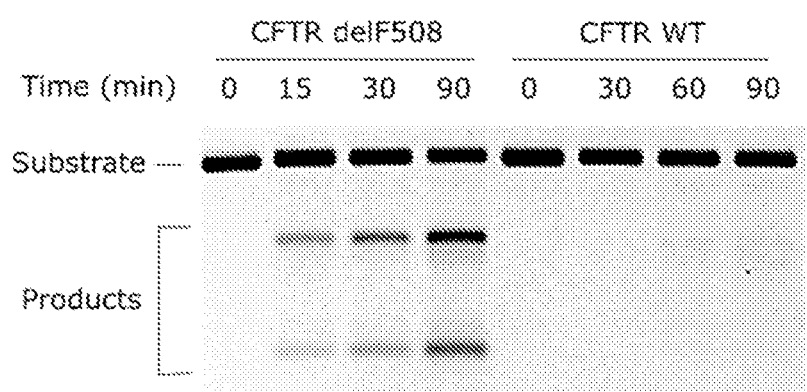
FIG. 5 evidences that TevCas9, targeted to the CFTR Delta F508 mutation using guide in SEQ ID 21, cleaves a DNA substrate containing the CFTR Delta F508 mutation, but not substrate containing the wild-type CFTR sequence in vitro.
Figure 6A:
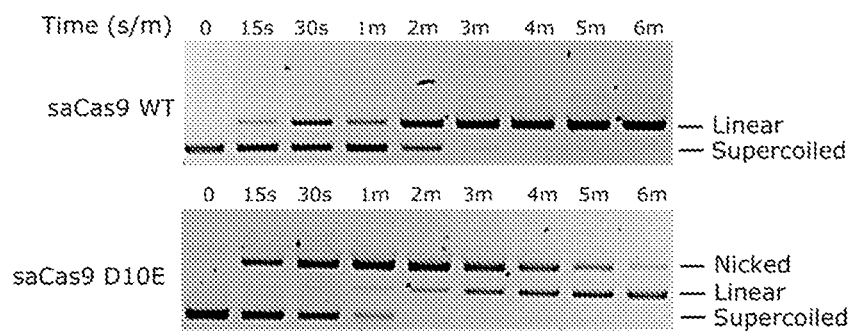
FIG. 6A illustrates that the saCas9 D10E mutation slows the conversion of nicked supercoiled DNA to linear DNA.
Figure 6B:
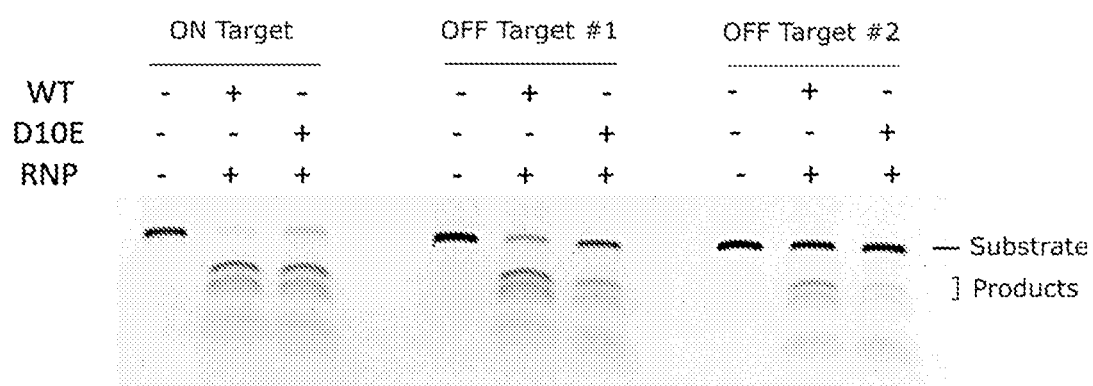
FIG. 6B evidences that on linear EMX1 DNA substrate, saCas9D10E (D10E) ribonucleoprotein complex (RNP) cleaves the target substrate to a similar level as saCas9 wild-type (WT). Levels of editing by SaCas9D10E at computationally predicted off-targets is lower than levels of editing by wild-type saCas9 at the same off-targets.
Figure 7A:
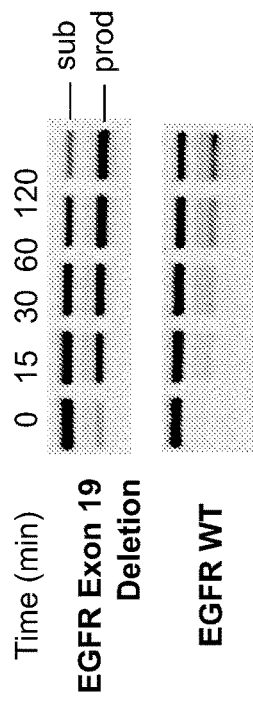
FIG. 7A is a schematic of spacing of the I-TevI sites in the EGFR Exon 19 deletion and wild-type (WT) EGFR.
Figure 7B:
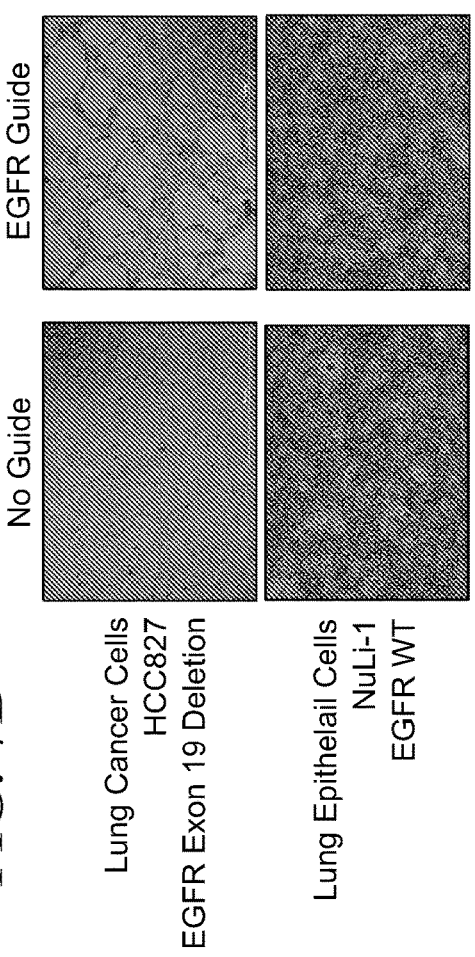
FIGS. 7B and 7C evidences that TevCas9 containing the nicking mutation in Cas9 (H557A) targeted to EGFR using the guide RNA in SEQ ID 16 cleaves EGFR Exon 19 deletion DNA substrate at a 4-fold faster rate than wild type EGFR.
Figure 7C:
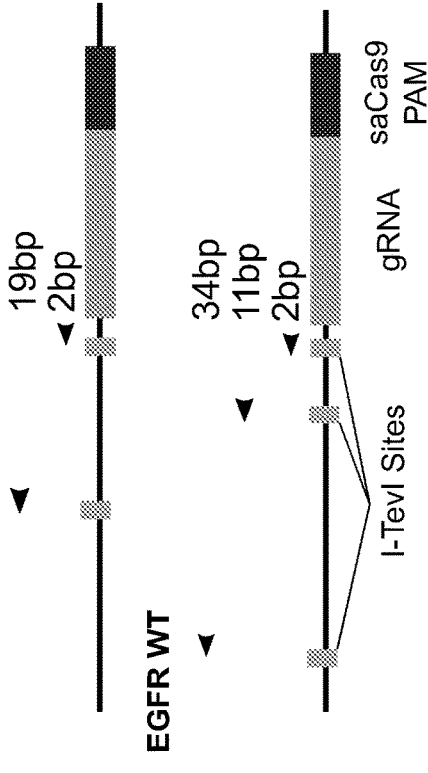
Figure 7D:
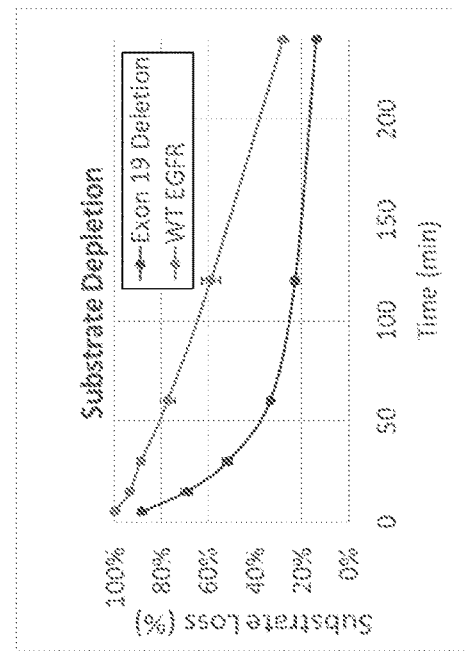
FIG. 7D are images of HCC827 cells harbouring the EGFR Exon 19 deletion mutation treated with TevCas9 targeted to EGFR are selectively killed compared to NuLi-1 cells harbouring wild-type EGFR (WT).

The instant invention is directed to a chimeric nuclease comprising a modified I-TevI nuclease domain, preferably deleting Met$^1$ and having Lys$^{26}$ (which is Lys$^{27}$ in the untruncated version of I-TevI) and/or Cys$^{39}$ (which is Cys$^{40}$ in the untruncated version of I-TevI) modification, a linker, in particular SEQ ID NOS: 7-12 or fragments thereof and/or containing one or more of the following mutations Thr$^{95}$ (as referenced to the full-length I-TevI), Val$^{117}$, Lys$^{135}$, Gln$^{158}$ or Asn$^{140}$, and a modified RNA-guided nuclease *Staphylococcus aureus* Cas9 that may be the wild-type or a modified version, preferably containing a Glu$^{10}$ or an Ala$^{557}$ mutation thereof wherein said I-TevI polypeptide comprises the entire amino acid sequence of SEQ ID NO: 6 or a fragment thereof, and guide RNA, in particular, SEQ ID NOS: 15, 16 or 21 or fragments thereof, that targets the Cas9 domain and a pharmaceutically-acceptable formulation comprising the chimeric nuclease, cationic and/or neutral lipid nanoparticles, optionally DNA-binding compounds, in particular GL67 (N$^4$-cholesteryl-spermine) and a pharmaceutically acceptable carrier thereof.

In a further embodiment of the instant invention, in the formulation the lipid nanoparticle may contain exogenous donor DNA.

Another embodiment of the invention is directed to methods to edit genes by administering a chimeric nuclease to a cell or organism without the use of a viral vector by using a controlled dose in vivo.

Another embodiment of the invention is directed to methods to delete defined lengths of a DNA molecule or to replace select sequences from a DNA molecule by delivering a chimeric nuclease in vivo to a whole organism or to isolated cells in culture ex vivo wherein said cells are mammalian cells, bacteria, insect cells or plant cells.

In yet another embodiment, the novel chimeric nuclease targets two independent target sites on a select DNA molecule either cleaving at one target site or at both target sites and creating fragments that are 30 to 36 nucleotides in length.

In a further example, the novel, purified chimeric nuclease further comprises a guide RNA.

Another aspect of the instant inventions is the use of an extrusion process creating particles of approximately 100 nM in diameter comprising an excipient wherein the excipient is selected from the group consisting of polysorbates, polyphosphates, calcium chlorides, sodium chloride, sodium citrates, sodium hydroxide, sodium phosphates, sodium ethylenediaminetetraacetic acid, potassium chloride, potassium phosphate and starches, or mixtures of these substances so that the novel chimeric nuclease can be administered to a patient using a nebulizer containing said formulation.

In a preferred embodiment, the instant invention is directed to a method of treating a lung-related disease in a patient in need thereof by administering a novel chimeric nuclease that modifies the DNA of lung epithelial cells wherein the chimeric nuclease replaces the CFTR delta F508 mutation from the CFTR gene in an effort to treat cystic fibrosis or cleaves an EGFR exon 19 deletion in an effort to treat non-small cell lung cancer.

In yet another embodiment, the invention is directed to a chimeric nuclease comprising a modified I-TevI nuclease domain, a linker and a modified RNA-guided nuclease *Staphylococcus aureus* Cas9 wherein said RNA-guided nuclease *Staphylococcus aureus* Cas9 contains Ala$^{10}$, Ala$^{557}$ or Ala$^{580}$ mutations and targets the EGFR exon 19 deletions of the EGFR gene.

In a further embodiment, wherein said guide RNA targets a specific CTFR gene sequence to cleave out the CFTR delta F508 mutation or a specific EGFR gene sequence that contains an EGFR exon 19 deletion mutation.

The instant invention also covers linkers comprising SEQ ID NOS: 7-12 or fragments thereof and modified donor DNA molecules selected from the group consisting of a linear single-strand of DNA comprising homologous regions flanking the sites targeted and/or cleaved by a chimeric nuclease, a linear double-strand DNA comprising homologous regions flanking the sites targeted and/or cleaved by a chimeric nuclease, a double strand DNA of the same length comprising complimentary DNA ends to those cleaved by a chimeric nuclease, a circular double-strand DNA comprising homologous regions flanking the sites targeted and/or cleaved by a chimeric nuclease, and a circular double-strand DNA comprising an I-TevI target site and a Cas9 target site wherein the product cleaved from the double-strand DNA contains complimentary ends to the ends cleaved by a chimeric nuclease.

In a further example consists of a chimeric nuclease comprising a modified GIY-YIG nuclease domain, a linker and a modified RNA-guided nuclease *Staphylococcus aureus* Cas9 or *Streptococcus pyogenes* Cas9 or EQR *Streptococcus pyogenes* Cas9 variant containing a Glu$^{10}$ mutation (SEQ ID NO:19) and/or a Ala$^{840}$ mutation and/or a mutation that cleaves the sugar phosphate backbone of a target DNA on one strand of a target DNA wherein said GIY-YIG nuclease domain is selected from the gene family consisting of I-BmoI and Eco29kI.

In yet a further embodiment, the instant invention includes a chimeric nuclease comprising a modified I-TevI nuclease domain, a linker and a modified nuclease or DNA targeting domain wherein said modified nuclease or DNA targeting domain is selected from the group consisting of LAGLIDADG, His-Cys Box, H—N—H, PD-(D/E)xK and Vsr-like meganucleases, zinc-finger nuclease, CRISPR protein selected from the group consisting of scCas9 (*Streptococcus canis*), fnCas9 (*Francisella novicida*), cjCas9 (*Campylobacter jejuni*), Cpf1 (*Lachnospiraceae bacterium*), Cas12a (*Acidaminococcus* Sp), Cas13a (*Leptorichia shahii*) and Cas3 (*Streptococcus thermophilus*) and DNA binding domain selected from the group consisting of zinc-finger motifs and TALE activator domains.

In an even further example, the instant invention covers a modified RNA-guided nuclease *Staphylococcus aureus* Cas9 and a guide RNA wherein said guide RNA contains sequences that target genetic polymorphisms, different sequences in the CFTR or EGFR genes, sequences that retarget a nuclease, bridged nucleic acids and/or a mixture of guide RNAs.

DETAILED DESCRIPTION OF THE INVENTION

Definitions and Acronyms

For convenience, certain terms employed in the specification, examples and appended claims are collected here. These definitions should be read in light of the disclosure and understood as by a person of skill in the art. Unless defined otherwise, all technical and scientific terms used herein have the same meaning as commonly understood by a person of ordinary skill in the art.

The articles "a" and "an" are used herein to refer to one or to more than one (i.e., to at least one) of the grammatical object of the article. The term "and/or" as used herein is defined as the possibility of having one or the other or both. For example, "A and/or B" provides for the scenarios of having just A or just B or a combination of A and B. If the claim reads A and/or B and/or C, the composition may include A alone, B alone, C alone, A and B but not C, B and C but not A, A and C but not B or all three A, B and C as components.

The term "bioavailable" is art-recognized and refers to a form of the subject disclosure that allows for it, or a portion of the amount administered, to be absorbed by, incorporated to, or otherwise physiologically available to a subject or patient to whom it is administered.

The term "exogenous donor DNA", as used herein, refers to any sequence of DNA that, in whole or in part, is not the same as the original target DNA sequence.

The term "flexible linker", as used herein, refers to a situation when the RNA-guided nuclease domain (Cas9) binds to the target DNA sequence, the amino acid linker domain ensures mobility of the I-TevI domain to allow for recognition, binding and cleaving of its target sequence under cell physiological conditions (typically: pH ~7.2, temperature ~37° C., [K+] ~140 mM, [Na+] ~5-15 mM, [Cl−] ~4 mM, [Ca++] ~0.0001 mM). The length of the amino acid linker can influence how many nucleotides are preferred between the Cas9 target site and the I-TevI target site. Certain amino acids in the linker may also make specific contacts with the DNA sequence targeted by TevCas9. These linker-DNA contacts can affect the flexibility of the I-TevI domain. Substituting amino acids in the linker domain may affect the ability of the linker domain to make contact with DNA.

The term "including", as used herein, is used to mean "including but not limited to". "Including" and "including but not limited to" are used interchangeably.

The terms "inhaled administration", "inhale", "inhaled", "inhalation" or "inhalation therapy", which may be used interchangeably and as used herein, include administration of a substantially uniform distribution of appropriately sized particles to the respiratory epithelium of the nose, central airways, the peripheral aspect of the lung and/or the alveolar region of the lung or by intratracheal instillation. Such particles may be introduced to the patient and/or produced using an appropriate device, preferably a nebulizer.

The term "patient," "subject" or "host" to be treated by the subject method may mean either a human or non-human animal. Non-human animals include companion animals (e.g. cats, dogs) and animals raised for consumption (i.e. food animals), such as cows, pigs, and chickens.

The term "pharmaceutically acceptable carrier" is art-recognized and refers to a pharmaceutically-acceptable material, composition or vehicle, such as a liquid or solid filler, diluent, excipient, solvent or encapsulating material, involved in carrying or transporting any subject composition or component thereof from one organ, or portion of the body, to another organ, or portion of the body. Each carrier must be "acceptable" in the sense of being compatible with the subject composition and its components and not injurious to the patient. Some examples of materials which may serve as pharmaceutically acceptable carriers include: (1) sugars, such as dextrose, lactose, glucose and sucrose; (2) starches, such as corn starch and potato starch; (3) cellulose, and its derivatives, such as microcrystalline cellulose, sodium carboxymethyl cellulose, methyl cellulose, ethyl cellulose, hydroxypropylmethyl cellulose (HPMC), and cellulose acetate; (4) glycols, such as propylene glycol; (5) polyols, such as glycerin, sorbitol, mannitol and polyethylene glycol; (6) esters, such as ethyl oleate, glyceryl behenate and ethyl laurate; (7) buffering agents, such as monobasic and dibasic phosphates, Tris/Borate/EDTA and Tris/Acetate/EDTA (8) pyrogen-free water; (9) isotonic saline; (10) Ringer's solution; (11) ethyl alcohol; (12) phosphate buffer solutions; (13) polysorbates; (14) polyphosphates; and (15) other non-toxic compatible substances employed in pharmaceutical formulations. The disclosed excipients may serve more than one function. For example, a solubilizing agent may also be a suspension aid, an emulsifier, a preservative, and the like.

In certain preferred embodiments, the pharmaceutically acceptable excipient is a crystalline bulking excipient. The terms "crystalline bulking excipient" or "crystalline bulking agent" as used herein means an excipient which provides bulk and structure to the lyophilization cake. These crystalline bulking agents are inert and do not react with the protein or nucleic acid. In addition, the crystalline bulking agents are capable of crystallizing under lyophilization conditions. Examples of suitable crystalline bulking agents include hydrophilic excipients, such as, water soluble polymers; sugars, such as mannitol, sorbitol, xylitol, glucitol, ducitol, inositiol, arabinitol, arabitol, galactitol, iditol, allitol, maltitol, fructose, sorbose, glucose, xylose, trehalose, allose, dextrose, altrose, lactose, glucose, fructose, gulose, idose, galactose, talose, ribose, arabinose, xylose, lyxose, sucrose, maltose, lactose, lactulose, fucose, rhamnose, melezitose, maltotriose, raffinose, altritol, their optically active forms (D- or L-forms) as well as the corresponding racemates; inorganic salts, both mineral and mineral organic, such as, calcium salts, such as the lactate, gluconate, glycerylphosphate, citrate, phosphate monobasic and dibasic, succinate, sulfate and tartrate, as well as the same salts of aluminum and magnesium; carbohydrates, such as, the conventional mono- and di-saccharides as well as the corresponding polyhydric alcohols; proteins, such as, albumin; amino acids, such as glycine; emulsifiable fats and polyvinylpyrrolidone. Preferred crystalline bulking agents are selected from the group consisting of glycine, mannitol, dextran, dextrose, lactose, sucrose, polyvinylpyrrolidone, trehalose, glucose and combinations thereof. Particularly useful bulking agents include dextran.

The term "pharmaceutically-acceptable salts", as used herein, is art-recognized and refers to the relatively non-toxic, inorganic and organic acid addition salts, or inorganic or organic base addition salts of compounds, including, for example, those contained in compositions of the present invention. Some examples of pharmaceutically-acceptable salts include: (1) calcium chlorides; (2) sodium chlorides; (3) sodium citrates; (4) sodium hydroxide; (5) sodium phosphates; (6) sodium ethylenediaminetetraacetic acid; (7) potassium chloride; (8) potassium phosphate; and (9) other non-toxic compatible substances employed in pharmaceutical formulations.

The term "substitution", as used herein, refers to the replacement of an amino acid in a sequence with a different amino acid. As used herein, the shorthand X10Y indicates that amino acid Y has been "substituted" for amino acid X found in the $10^{th}$ position of the sequence. As an example, W26C denotes that amino acid Tryptophan-26 (Trp, W) is changed to a Cysteine (Cys). Similarly, the notation $AA^X$ indicates that AA is an amino acid that replaced the amino acid found in the X position. As an example, $Lys^{26}$ denotes the replacement of the amino acid in the $26^{th}$ position in a sequence with Lysine. Use of either shorthand is interchangeable. In addition, use of the one- or three-letter abbreviations for an amino acid is also interchangeable.

The term "therapeutic agent", as used herein, is art-recognized and refers to any chemical or biochemical moiety that is a biologically, physiologically, or pharmacologically active substance that acts locally or systemically in a subject. Examples of therapeutic agents, also referred to as "drugs", are described in well-known literature references such as the Merck Index, the Physician's Desk Reference, and The Pharmacological Basis of Therapeutics, and they include, without limitation, medicaments; vitamins; mineral supplements; substances used for the treatment, prevention, diagnosis, cure or mitigation of a disease or illness; substances which affect the structure or function of the body; or pro-drugs, which become biologically active or more active after they have been placed in a physiological environment.

The term "therapeutic effect", as used herein, is art-recognized and refers to a local or systemic effect in animals, particularly mammals, and more particularly humans caused by a pharmacologically active substance. The term thus means any substance intended for use in the diagnosis, cure, mitigation, treatment, or prevention of disease or in the enhancement of desirable physical or mental development and/or conditions in an animal or human. The phrase "therapeutically-effective amount" means that amount of such a substance that produces some desired local or systemic effect at a reasonable benefit/risk ratio applicable to any treatment. The therapeutically effective amount of such substance will vary depending upon the subject and disease condition being treated, the weight and age of the subject, the severity of the disease condition, the manner of administration and the like, which can readily be determined by one of ordinary skill in the art. For example, certain compositions of the present invention may be administered in a sufficient amount to produce a at a reasonable benefit/risk ratio applicable to such treatment.

The term "treating", as used herein, includes any effect, e.g., lessening, reducing, modulating, or eliminating, that results in the improvement of the condition, disease, disorder, and the like. As used herein, "treating" can include both prophylactic, and therapeutic treatment. For example, therapeutic treatment can include delaying inhibiting or preventing the progression of cystic fibrosis or non-small cell lung cancer, the reduction or elimination of symptoms associated with cystic fibrosis or non-small cell lung cancer. Prophylactic treatment can include preventing, inhibiting or delaying the onset of cystic fibrosis or non-small cell lung cancer.

As used herein, an "effective amount" refers to an amount sufficient to elicit the desired response. In the present invention, the desired biological response is the treatment of cystic fibrosis and/or non-small cell lung cancer (NSCLC).

A "buffer" as used herein is any acid or salt combination which is pharmaceutically acceptable and capable of maintaining the composition of the present invention within a desired pH range. Buffers in the disclosed compositions maintain the pH in a range of about 2 to about 8.5, about 5.0 to about 8.0, about 6.0 to about 7.5, about 6.5 to about 7.5, or about 6.5. Suitable buffers include, any pharmaceutical acceptable buffer capable of maintaining the above pH ranges, such as, for example, acetate, tartrate phosphate or citrate buffers. In one embodiment, the buffer is a phosphate buffer. In another embodiment the buffer is an acetate buffer. In one embodiment the buffer is disodium hydrogen phosphate, sodium chloride, potassium chloride and potassium phosphate monobasic.

In the disclosed compositions the concentration of buffer is typically in the range of about 0.1 mM to about 1000 mM, about 0.2 mM to about 200 mM, about 0.5 mM to about 50 mM, about 1 mM to about 10 mM or about 6.0 mM.

As used herein, an "anti-microbial agent" is a pharmaceutically acceptable preservative, suitable for administration to a subject, which inhibits, prevents, or delays the growth or microorganisms including, for example bacteria, viruses and fungi in the compositions of the present invention. Suitable anti-microbial agents for use in the compositions and methods of the present invention include, but are not limited to, cresols, benzyl alcohol, phenol, benzalkonium chloride, benzethonium chloride, chlorobutanol, phenylethyl alcohol, methyl paraben, propyl paraben, thiomersal and phenylmercuric nitrate and acetate. In one embodiment the anti-microbial agents is m-cresol, chlorocresol or phenol. In another embodiment the anti-microbial agents is chlorocresol or phenol. In another embodiment the anti-microbial agents is phenol.

As used herein an effective amount of an anti-microbial agent is an amount effective to inhibit, prevent or delay the growth or microorganisms including, for example bacteria, viruses, and fungi in the compositions of the present invention. In the compositions of the present invention, the amount of anti-microbial agent is typically in the range from about 0.1 to about 20 mg/ml, about 0.2 to about 30 mg/ml, about 0.2 to about 10 mg/ml, about 0.25 to about 5 mg/ml, about 0.5 to about 50 mg/ml, about 1 to about 10 mg/ml, about 3 mg/ml or about 5 mg/ml.

The compositions of the present invention can also be lyophilized using lyophilization techniques known in the art and stored as a powder which can be reconstituted prior to administration. The term "lyophilization" as used herein is a freeze drying or dehydration technique which involves removing a solvent, preferably a water miscible solvent, more preferably water from a composition or the present invention, typically by sublimation under high vacuum when the composition is in a frozen state. Typically, lyophilization is carried out in lyophilization equipment (a lyophilizer), which comprises a drying chamber with variable temperature controls, a condenser to collect water, and a vacuum system to reduce the pressure in the drying chamber.

The terms "lyophilized composition", as used herein mean the solid residue or powder which is produced, or which remains after the lyophilization procedure as defined above. The lyophilized composition of the present invention typically further comprises a pharmaceutically acceptable excipient. The term "pharmaceutically acceptable excipient" as used herein refers to a substance which is added to a solution prior to lyophilization to enhance characteristics such as the color, texture, strength, and volume of the lyophilized cake. Pharmaceutically acceptable excipients may be, for example, buffers and pH adjusters, crystalline bulking excipients, stabilizers, and tonicity raising agents.

As used herein, a stabilizer is a composition which maintains the chemical, biological or stability of the chimeric nuclease. Examples of stabilizing agent include polyols, which includes a saccharide, preferably a monosaccharide or disaccharide, e.g., glucose, trehalose, raffinose, or sucrose; a sugar alcohol such as, for example, mannitol, sorbitol or inositol, a polyhydric alcohol such as glycerin or propylene glycol or mixtures thereof and albumin.

A pharmaceutically acceptable salt is a salt which is suitable for administration to a subject, such as, a human. The chimeric nuclease of the present invention can have one or more sufficiently acidic proton that can react with a suitable organic or inorganic base to form a base addition salt. Base addition salts include those derived from inorganic bases, such as ammonium or alkali or alkaline earth metal hydroxides, carbonates, bicarbonates, and the like, and organic bases such as alkoxides, alkyl amides, alkyl and aryl amines, and the like. Such bases useful in preparing the salts of this invention thus include sodium hydroxide, potassium hydroxide, ammonium hydroxide, potassium carbonate, and the like. The chimeric nuclease of the present invention having a sufficiently basic group, such as an amine can react with an organic or inorganic acid to form an acid addition salt. Acids commonly employed to form acid addition salts from compounds with basic groups are inorganic acids such as hydrochloric acid, hydrobromic acid, hydroiodic acid, sulfuric acid, phosphoric acid, and the like, and organic acids such as p-toluenesulfonic acid, methanesulfonic acid, oxalic acid, p-bromophenyl-sulfonic acid, carbonic acid, succinic acid, citric acid, benzoic acid, acetic acid, and the like. Examples of such salts include the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, gamma-hydroxybutyrate, glycolate, tartrate, methanesulfonate, propanesulfonate, naphthalene-1-sulfonate, naphthalene-2-sulfonate, mandelate, and the like.

While specific embodiments of the subject invention have been discussed, the above specification is illustrative and not restrictive. Many variations of the invention will become apparent to those skilled in the art upon review of this specification. The full scope of the invention should be determined by reference to the claims, along with their full scope of equivalents, and the specification, along with such variations.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specification and attached claims are approximations that may vary depending upon the desired properties sought to be obtained by the present invention.

The above discussion is meant to be illustrative of the principle and various embodiments of the present invention. Numerous variations and modifications will become apparent to those skilled in the art once the above disclosure is fully appreciated. It is intended that the following claims be interpreted to embrace all such variations and modifications.

Abbreviations

Abbreviations used herein are defined as follows:
AA amino acid
Cas9 CRISPR-associated protein 9

CF Cystic fibrosis
CFTR Cystic fibrosis transmembrane conductance regulator gene
cjCas9 *Campylobacter jejuni* Cas9
Cpf1 CRISPR from *Prevotella* and *Francisella* 1
CRISPR Clustered Regulatory Interspaced Short Palindromic Repeats
DLS Dynamic Light Scattering
DMEM Dulbecco's Modified Eagle's Medium
DMPE 1,2-ditetradecanoyl-sn-glycero-3-phosphoethanolamine
DNA deoxyribonucleic acid
DOAB dioctadecyldimethylammonium bromide
DOPE 1,2-Dioleoyl-sn-glycero-3-phosphoethanolamine
DPPC Dipalmitoylphosphatidylcholine
*E. coli Escherichia coli*
EDTA ethylenediaminetetraacetic acid
EGFR Epidermal growth factor receptor
ELISA Enzyme-linked immunosorbent assay
fnCas9 *Francisella novicida* Cas9
HDR Homology directed repair
IMAC Immobilized Metal Affinity Chromatography
IPTG Isopropyl β-D-1-thiogalactopyranoside
MPEG-5000-DMPE N-(carbonyl-methoxypolyethyleneglycol 5000)-1,2 dipalmitoyl-sn-glycero-3-phosphoethanolamine
NSCLC Non-small cell lung cancer
NHEJ Non-homologous end joining
NLS Nuclear-localized signal
PC Phosphatidylcholine
PCR polymerase chain reaction
PE Phosphoethanolamine
RNA ribonucleic acid
saCas9 *Staphylococcus aureus* Cas9
scCas9 *Streptococcus canis* Cas9
SDS sodium dodecyl sulfate
spCas9 *Streptococcus pyogenes* Cas9
TALEN Transcription activator-like effector nucleases
TEV Tobacco Etch Virus
TevCas9 Modified I-TevI domain, a linker peptide and modified RNA-guided nuclease *Staphylococcus aureus* Cas9
ZFN zinc-finger nucleases The Inventors discovered a chimeric nuclease comprising a modified version of an I-TevI domain, a linker peptide and a modified version of an RNA-guided nuclease *Staphylococcus aureus* Cas9 ("saCas9") (hereinafter referred to as "TevCas9") that, when mixed with a lipid nanoparticle, with or without exogenous donor DNA, when delivered to cells, replaces DNA sequences in the presence of exogenous donor DNA or deletes defined lengths of DNA in the absence of exogenous donor DNA. The novel chimeric nuclease has been shown to edit genes in human cells, but also cells of other organisms such as bacteria, yeast, insect, plant, or other mammals, either in whole organisms (in vivo) or in isolated cells cultures (ex vivo).

The novel chimeric nucleases discovered by the present Inventors present the following advantages over existing gene editing technologies and methods, in particular,
a. The nuclease, which is a modified version of the TevCas9 nuclease, is capable of targeting two independent target sites as a single protein and cleaving the DNA at one or both of these sites. It can be reprogrammed to many different target DNA sequences through modifying one or more of the I-TevI domain, the linker domain, the Cas9 domain or the guide RNA (which targets the Cas9 domain to its target sequence);
b. If the nuclease cleaves at two sites, it cleaves out precise lengths of DNA (~30-36 bases depending on the sites targeted by I-TevI and Cas9);
c. The Cas9 domain contains a mutation (D10E) which is rationally designed to modify the Cas9 nuclease activity and/or increase the Cas9 domain's specificity for its target binding site;
d. In the presence of exogenous donor DNA, the invention is designed to replace target DNA sequences in a higher percentage of cells than existing technologies or practices;
e. The nuclease can be purified as a single contiguous protein combined with a guide RNA, which simplifies manufacturing;
f. The lipid nanoparticle allows for non-viral delivery to target cells with high efficiency and low toxicity, allowing for controlled dosing of the nuclease. Although other lipid-based nuclease delivery technologies exist, none are of a composition suitable for use in vivo;
g. The lipid nanoparticles are also designed for the delivery of nuclease through nebulization (inhalation);
h. One version of the nuclease targets and cleaves the CFTR gene to correct the CFTR delta F508 mutation for the treatment of Cystic Fibrosis (SEQ ID NO 1); and
i. Another version of the nuclease is designed to target and cleave the clinically relevant EGFR exon 19 deletion mutations (SEQ ID NOS 2-4), which are present in a variety of cancers, including non-small-cell lung cancer (NSCLC).

The fusion of a GIY-YIG nuclease, such as I-TevI, through a flexible linker to DNA binding domains is known (WO2014/121222). A prior version of the dual-cleaving TevCas9 has been described which comprises amino acids 1-92 of the wild-type I-TevI nuclease domain, a linker region comprising amino acids 93-169 of I-TevI linker region and the *Streptococcus pyogenes* Cas9 ("spCas9") (Wolfs J M et al., (2016), 'Biasing Genome-Editing Events Toward Precise Length Deletions with an RNA-Guided TevCas9 Dual Nuclease,' *Proc Natl Acad Sci USA*, 113(52): 14988-93). The chimeric nuclease of the invention comprises the following:
i. An I-TevI nuclease domain which binds a new target sequence allowing to target clinically relevant gene sequences, such as the CFTR gene;
ii. Various flexible linker regions intended to confer different DNA binding or nuclease activity to TevCas9;
iii. A saCas9 nuclease domain (US-1988/065406 B2). The use of saCas9 over spCas9 results in a smaller DNA coding sequence (~3.7 kilobases for Tev-saCas9 versus ~4.6 kilobases for Tev-spCas9) and lower molecular weight TevCas9 protein (~144 kilodaltons for Tev-saCas9 versus ~179 kilodaltons for Tev-spCas9) which is more amenable to multiple delivery technologies; cleaving by the saCas9 domain between the $3^{rd}$ and $4^{th}$ nucleotide is predictable compared to spCas9 which is more amenable to defined length deletions, as discovered by the inventors of the claimed technology.
iv. One version where the guide RNA is targeted to specific CFTR gene sequence near the CFTR delta F508 mutation; and
v. A second version where the guide RNA is targeted to specific EGFR gene sequences and is intended to cleave only DNA with appropriated spaced I-TevI site and Cas9 target site. Such appropriately spaced sites occur in certain EGFR exon 19 deletion mutations (SEQ ID NO 2-4) but not in wild-type EGFR (SEQ ID NO 5);

a. The invention comprises lipid nanoparticles of certain compositions that are selectively sized to a mean diameter of approximately 100 nM. These lipid nanoparticles are capable of delivering the nuclease to cells with high efficiency and low toxicity;
b. A pharmaceutical formulation of the lipids, nuclease, and exogenous donor DNA;
c. A pharmaceutical formulation of the lipids, nuclease and exogenous donor DNA which is suitable for nebulization (inhalation); and
d. A version of the invention which contains exogenous donor DNA that when delivered with the TevCas9 nuclease in the lipid nanoparticle is capable of integrating into the region between or around the two sites targeted by the nuclease.

The novel chimeric nuclease compositions of the instant application contain different combinations of an I-TevI domain, a linker domain, a Cas9 domain and a guide RNA.

The versions that target the CFTR gene are comprised of:
i. An I-TevI domain of amino acid sequence according to SEQ ID NO: 6;
ii. A linker domain according to any one of SEQ ID NOS: 7-12;
iii. A saCas9 domain of the amino acid sequence according to SEQ ID NO: 13; and
iv. A guide RNA of the RNA sequence according to SEQ ID NO: 15 or 21.

The versions that target the EGFR gene are comprised of:
i. An I-TevI domain of amino acid sequence according to SEQ ID NO: 6;
ii. A linker domain with any one of the amino acid sequences according to SEQ ID NO 7-12;
iii. A saCas9 domain of the amino acid sequence according to SEQ ID NO: 13; and
iv. A guide RNA of the RNA sequence in SEQ ID NO: 16.

The I-TevI domain of the preferred embodiment is a 93-amino acid I-TevI domain of the Enterobacteria Phage T4 according to the following sequence:

```
                                          (SEQ ID NO: 6)
MGKSGIYQIKNTLNNKVYVGSAKDFEKRWKRHFKDLEKGCHSSIKLQRS
FNKHGNVFECSILEEIPYEKDLIIERENFWIKELNSKINGYNIA
```

The saCas9 of the preferred embodiment is a polypeptide comprised of 1,053 amino acids according to the following sequence:

```
                                          (SEQ ID NO: 13)
MKRNYILGLDIGITSVGYGIIDYETRDVIDAGVRLFKEANVENNEGRRS
KRGARRLKRRRRHRIQRVKKLLFDYNLLTDHSELSGINPYEARVKGLSQ
KLSEEEFSAALLHLAKRRGVHNVNEVEEDTGNELSTKEQISRNSKALEE
KYVAELQLERLKKDGEVRGSINRFKTSDYVKEAKQLLKVQKAYHQLDQS
FIDTYIDLLETRRTYYEGPGEGSPFGWKDIKEWYEMLMGHCTYFPEELR
SVKYAYNADLYNALNDLNNLVITRDENEKLEYYEKFQHIENVFKQKKKP
TLKQIAKEILVNEEDIKGYRVTSTGKPEFTNLKVYHDIKDITARKEIIE
NAELLDQIAKILTIYQSSEDIQEELTNLNSELTQEEIEQISNLKGYTGT
HNLSLKAINLILDELWHTNDNQIAIFNRLKLVPKKVDLSQQKEIPTTLV
DDFILSPVVKRSFIQSIKVINAIIKKYGLPNDIIIELAREKNSKDAQKM
INEMQKRNRQTNERIEEIIRTTGKENAKYLIEKIKLHDMQEGKCLYSLE
AIPLEDLLNNPFNYEVDHIIPRSVSFDNSFNNKVLVKQEENSKKGNRTP
FQYLSSSDSKISYETFKKHILNLAKGKGRISKTKKEYLLEERDINRFSV
QKDFINRNLVDTRYATRGLMNLLRSYFRVNNLDVKVKSINGGFTSFLRR
KWKFKKERNKGYKHHAEDALIIANADFIFKEWKLDKAKKVMENQMFEEK
QAESMPEIETEQEYKEIFITPHQIKHIKDFKDYKYSHRVDKKPNRELIN
DTLYSTRKDDKGNTLIVNNLNGLYDKDNDKLKKLINKSPEKLLMYHHDP
QTYQKLKLIMEQYGDEKNPLYKYYEETGNYLTKYSKKDNGPVIKKIKYY
GNKLNAHLDITDDYPNSRNKVVKLSLKPYRFDVYLDNGVYKFVTVKNLD
VIKKENYYEVNSKCYEEAKKLKKISNQAEFIASFYNNDLIKINGELYRV
IGVNNDLLNRIEVNMIDITYREYLENMNDKRPPRIIKTIASKTQSIKKY
STDILGNLYEVKSKKHPQIIKKG
```

The saCas9 with a Glu[10] mutation of the preferred embodiment is a polypeptide comprised of 1,053 amino acids according to the following sequence (the mutation is underlined):

```
                                          (SEQ ID NO: 14)
MKRNYILGLEIGITSVGYGIIDYETRDVIDAGVRLFKEANVENNEGRRS
KRGARRLKRRRRHRIQRVKKLLFDYNLLTDHSELSGINPYEARVKGLSQ
KLSEEEFSAALLHLAKRRGVHNVNEVEEDTGNELSTKEQISRNSKALEE
KYVAELQLERLKKDGEVRGSINRFKTSDYVKEAKQLLKVQKAYHQLDQS
FIDTYIDLLETRRTYYEGPGEGSPFGWKDIKEWYEMLMGHCTYFPEELR
SVKYAYNADLYNALNDLNNLVITRDENEKLEYYEKFQHIENVFKQKKKP
TLKQIAKEILVNEEDIKGYRVTSTGKPEFTNLKVYHDIKDITARKEIIE
NAELLDQIAKILTIYQSSEDIQEELTNLNSELTQEEIEQISNLKGYTGT
HNLSLKAINLILDELWHTNDNQIAIFNRLKLVPKKVDLSQQKEIPTTLV
DDFILSPVVKRSFIQSIKVINAIIKKYGLPNDIIIELAREKNSKDAQKM
INEMQKRNRQTNERIEEIIRTTGKENAKYLIEKIKLHDMQEGKCLYSLE
AIPLEDLLNNPFNYEVDHIIPRSVSFDNSFNNKVLVKQEENSKKGNRTP
FQYLSSSDSKISYETFKKHILNLAKGKGRISKTKKEYLLEERDINRFSV
QKDFINRNLVDTRYATRGLMNLLRSYFRVNNLDVKVKSINGGFTSFLRR
KWKFKKERNKGYKHHAEDALIIANADFIFKEWKLDKAKKVMENQMFEEK
QAESMPEIETEQEYKEIFITPHQIKHIKDFKDYKYSHRVDKKPNRELIN
DTLYSTRKDDKGNTLIVNNLNGLYDKDNDKLKKLINKSPEKLLMYHHDP
QTYQKLKLIMEQYGDEKNPLYKYYEETGNYLTKYSKKDNGPVIKKIKYY
GNKLNAHLDITDDYPNSRNKVVKLSLKPYRFDVYLDNGVYKFVTVKNLD
VIKKENYYEVNSKCYEEAKKLKKISNQAEFIASFYNNDLIKINGELYRV
IGVNNDLLNRIEVNMIDITYREYLENMNDKRPPRIIKTIASKTQSIKKY
STDILGNLYEVKSKKHPQIIKKG
```

The guide RNA of the version that targets the CFTR gene is comprised of 101 ribonucleotides according to the sequences:

(SEQ ID NO: 15)
GCGUCAUCAAAGCAUGCCAACGUUUUAGUACUCUGGAAACAGAAUCUAC
UAAAACAAGGCAAAAUGCCGUGUUUAUCUCGUCAACUUGUUGGCGAGAU
UUU (SEQ ID NO: 21)
AUAUCAUUGGUGUUUCCUAUGGUUUUAGUACUCUGGAAACAGAAUCUAC
UAAAACAAGGCAAAAUGCCGUGUUUAUCUCGUCAACUUGUUGGCGAGAU
UUU

The guide RNA of the version that targets the EGFR gene is 101 ribonucleotides in length according to the following sequence:

(SEQ ID NO: 16)
AAUUUUAACUUUCUCACCUUCGUUUUAGUACUCUGGAAACAGAAUCUAC
UAAAACAAGGCAAAAUGCCGUGUUUAUCUCGUCAACUUGUUGGCGAGAU
UUU.

The linkers used in any of the above constructs may be selected from the group consisting of:

| SEQUENCE (amino acid count) | MUTATION(S) (indicated by underline) | SEQ ID NO: |
|---|---|---|
| DATFGDTCSTHPLKEEIIKKRSETFKAKMLKLGPDGRKALYSKPGSK NGRWNPETHKFCKCGVRIQTSAYTCSKCRNGGSGGS (83 AA) | V117F | 7 |
| DATFGDTCSTHPLKEEIIKKRSETVKAKMLKLGPDGRKALYSRPGSK SGRWNPETHKFCKCGVRIQTSAYTCSKCRNGGSGGS (83 AA) | K135R N140S | 8 |
| DATFGDTCSTHPLKEEIIKKRSETFKAKMLKLGPDGRKALYSRPGSKS GRWNPETHKFCKCGVRIQTSAYTCSKCRNGGSGGS (83 AA) | V117F K135R N140S | 9 |
| DATFGDTCSTHPLKEEIIKKRSETFKAKMLKLGPDGRKALYSRPGSKS GRWNPETHKFCKCGVRIQTSAYTCSKCRGGSGGTGGS (86 AA) | K135R N140S | 10 |
| DATFGDTCSTHPLKEEIIKKRSETFKAKMLKLGPDGRKALYSRPGSKS GRWNPETHKFCKCGVRIQTSAYTCSKCRGGGGSGGGGS (87 AA) | K135R N140S | 11 |
| DATFGDTCSTHPLKEEIIKKRSETFKAKMLKLGPDGRKALYSRPGSKS GRWNPETHKFCKCGVRIQTSAYTCSKCRKESGSVSSEQLAQFRSLD (95 AA) | K135R N140S | 12 |

Synthesis

Example 1: A Method to Manufacture the TevCas9 Nuclease

The DNA coding sequences of the above mentioned I-TevI domain, linker domain and Cas9 domain are synthesized as one contiguous DNA sequence using techniques known in the art. Gene synthesis was conducted by Bio Basic Inc. (Markham, On, Canada). Briefly, short oligonucleotides (~50-60 base pairs) are synthesized which contain regions of overlap to cover the entire sequences of I-TevI domain, linker domain and Cas9 domain. The oligonucleotides are mixed together in blocks of approximately 1 kilobase of the sequence to be synthesized and polymerase chain reaction (PCR) is used to synthesize these ~1 kilobase blocks. The ~1 kilobase blocks are then mixed and subjected to PCR to synthesis the I-TevI domain, linker domain and Cas9 domain. Further, to enhance expression of TevCas9 in E. coli and simplify restriction enzyme digestion, the DNA sequence of TevCas9 was optimized prior to synthesis. First, three-base pair DNA codons that are infrequently used by Escherichia coli ("E. coli") were replaced with those that occur more frequently (for example, of the 6 codons coding for the amino acid arginine, the relative abundance of the codon AGG is 0.03 compared to 0.42 for the codon CGT). In total, 37% of the codons were changed to those preferred by E. coli. Second, the content on the nucleotides cytosine and guanine was increased from 39.6% to 48.6%. Third, two E. coli ribosome binding sites were removed from the sequence. Fourth, a NdeI restriction endonuclease site was removed from the internal sequence. The contiguous DNA is digested with the restriction endonucleases NdeI and BamHI (New England Biolabs, Ipswich, Mass., United States), whose target sites occur only once in the DNA sequence, and then inserted using DNA ligase (New England Biolabs, Ipswich, Mass., United States) into a similarly digested pET-11a expression vector (EMD Millipore, Burlington, Mass., United States) suitable for expression of TevCas9 in E. coli. The pET-11a vector containing TevCas9 is transformed into the E. coli expression strain T7 Express (New England Biolabs #C2566, Ipswich, Mass., United States) which has been optimized for expression of proteins, including nucleases. Alternatively, the E. coli expression strain BL-21(DE3) (New England Biolabs #C2527, Ipswich, Mass., United States) is used. Successful transformations are confirmed by resistance of the E. coli to ampicillin or tetracycline and the coding sequence of TevCas9 is verified by DNA sequencing of the expression vector derived from the transformed E. coli. The transformed E. coli is grown at 37° C. to an optical density of 0.4 to 0.6 as measure by spectrophotometry at a wavelength of 600 nM and the expression of the TevCas9 protein from the pET-11a vector in the transformed E. coli expression strain is induced using IPTG for 10-12 hours at 16° C. Successful expression of TevCas9 is verified by the presence of an approximately 150 kDa band on a Coomassie-stained SDS-polyacrylamide gel in a sample of the induced material compared to the uninduced sample. The E. coli cells are harvested by centrifugation and resuspended in lysis buffer comprising 10 mM imidazole (Sigma, St. Louis, Mo., United States), 300-500 mM sodium chloride (Sigma-Aldrich, St. Louis, Mo., United States) and 50 mM sodium phosphate (dibasic) (Sigma, St. Louis, Mo., United States), pH 8.0 [Buffer 1]. Alternatively, 10 mM Tris Hydrochloride (Sigma, St. Louis, Mo., United States), pH 8 is substituted for substituted for sodium phosphate (dibasic) in Buffer 1. The E. coli is lysed by homogenization using a high pressure liquid, homogenizer (Avestin Inc., Ottawa, ON, Canada) operated at 600-1000 bar, or any other suitable lysis method known in the art, such as sonication using a sonifier (Branson Ultrasonics Corp, Danbury, Conn., United States) lysozyme treatment, homogenization using a French pressure cell (Glen Mills Inc., Clifton, N.J., United States) or homogenization using a Dounce homogenizer (Corning Inc., Corning, N.Y., United States). The lysed material is centrifuged at 12,000 rpm at 4° C. for 20-30 mins and the supernatant containing soluble TevCas9 is used for the subsequent purification steps. The pellet contains cell debris, insoluble intracellular material, as well as any insoluble TevCas9. Successful lysis and solubility is verified by the presence of an approximately 150 kDa band on a Coomassie-stained SDS-polyacrylamide gel in a sample of the supernatant when compared to a resuspended sample of the pellet.

The TevCas9 nuclease is purified in the following steps:
1. The lysate containing the nuclease is applied to an immobilized metal affinity chromatography (IMAC) column (GE Healthcare Bio-Sciences AB, Uppsala, Sweden) which binds the nuclease.
2. The IMAC column is washed with Buffer 1.
3. The TevCas9 remaining bound to the column is eluted with a solution comprising 250 mM imidazole (Sigma, St. Louis, Mo., United States), 300 mM-500 mM sodium chloride (Sigma-Aldrich, St. Louis, Mo., United States) and 50 mM sodium phosphate (dibasic) (Sigma, St. Louis, Mo., United States), pH 7.6-8.0 [Buffer 2]. Alternatively, 10 mM Tris Hydrochloride (Sigma, St. Louis Mo., United States), pH 7.6-8 is substituted for substituted for sodium phosphate (dibasic) in Buffer 2.
4. The eluate is treated with Tobacco Etch Virus (TEV) protease (New England Biolabs, Ipswich, Mass., United States) and incubated with the appropriate guide RNA. The guide RNA is synthesized by Integrated DNA Technology Inc. (Coralville, Iowa, United States).
5. The treated eluate is re-applied to the IMAC column and the flow-through containing the TevCas9 nuclease and guide RNA is collected.
6. Successful purification of the TevCas9 nuclease is confirmed by the presence of a 150 kilodalton protein band on a Coomassie-stained SDS-polyacrylamide gel. Successful co-purification of TevCas9 with the guide RNA is confirmed by treating a sample of the eluate with Proteinase K (New England Biolabs, Ipswich, Mass., United States), then splitting the sample in two and further treating one subsample with RNase A (New England Biolabs, Ipswich, Mass., United States) and the other in control buffer without RNase A. A ~100 nucleotide RNA band will be visible on an urea-polyacrylamide gel in the control sample and will be absent in the RNase A-treated sample.
7. The solution containing the TevCas9 nuclease and guide RNA is dialyzed into a solution comprising phosphate buffered saline, pH 7.4.

Example 2: A Method to Manufacture the Lipid Nanoparticles

The lipid nanoparticles of the preferred embodiment are comprised of one of the following mixtures:
I. Lipid nanoparticle No. 1 comprises DOPE (Avanti Polar Lipids, Alabaster, Ala., United States) and MPEG-5000-DMPE (Avanti Polar Lipids, Alabaster, Ala., United States) in a molar ratio of 2:0.05, respectively;

II. Lipid nanoparticle No. 2 comprises DPPC (Avanti Polar Lipids, Alabaster, Ala., United States), cholesterol (SUPELCO, Bellefonte, Pa., United States) and DOBA (Sigma, St. Louis, Mo., United States) in a molar ratio of 7:2:1, respectively; and
III. Lipid nanoparticle No. 3 comprised DPPC, cholesterol and MPEG-5000-DMPE (Avanti Polar Lipids, Alabaster, Ala., United States) in a molar ratio of 4:1:0.125, respectively.

Lipid nanoparticles are manufactured to a mean diameter of approximately 100 nM.

One of the lipid mixtures No. 1-3 is selected. For example, DOPE and MPEG-5000-DMPE are mixed together in the appropriate molar ratios in an organic solvent, such as chloroform. The organic solvent is then evaporated and the dried lipid mixture is re-suspended using vigorous vortexing in a solution comprising phosphate buffered saline, pH 7.4. The re-suspended lipid mixture is then extruded through a 100 nM polycarbonate membrane (T&T Scientific Corporation, Knoxville, Tenn., United States) equilibrated in phosphate buffered saline to create lipid nanoparticles of an approximate mean diameter of 100 nM. The solution is filter sterilized through 0.2 µM sterile filter (VWR Scientific, Radnor, Pa., United States). The mean diameter and size distribution of the lipid nanoparticles is determined by Dynamic Light Scattering (DLS) using a Zetasizer (Malvern Panalytical Ltd, Malvern, United Kingdom), or another suitable technique, known in the art.

Example 3: Composition of the Donor DNA

The donor DNA comprises DNA sequences that are intended to repair a genetic defect. It also comprises DNA sequences which are not found in the target genomic DNA; these sequences do not interfere with the normal gene function but are intended to knockout the I-TevI and or Cas9 sites and/or introduce one or more DNA sequences which are used to track the successful repair of the target gene. Examples of donor DNA include, but are not limited to the following:
I. Linear single-strand DNA of varying lengths comprising homologous regions flanking the sites targeted/cleaved by TevCas9;
II. Linear double-strand DNA of varying lengths comprising homologous regions flanking the sites targeted/cleaved by TevCas9;
III. Double-strand DNA of the same length cleaved by the nuclease and also comprising complimentary DNA ends to those cleaved by TevCas9;
IV. Circular double-strand DNA comprising homologous regions flanking the sites targeted/cleaved by TevCas9; and
V. Circular double-strand DNA comprising an I-TevI target site and Cas9 target site where the product cleaved from the double-strand DNA contains complimentary ends to those cleaved by TevCas9.

Example 4: A Method for Assembling the Lipid-Encapsulated TevCas9 and Transfecting Cells For ex vivo cell transfections: To assemble the lipid-encapsulated TevCas9, a lipid nanoparticle is mixed with the TevCas9 in a 2000:1 molar ratio in Dulbecco's Modified Eagle's Medium (DMEM) (Sigma, St. Louis, Mo., United States) and incubated at room temperature for 10 minutes. Cells are transfected with $8.7 \times 10E-17$ to $3.1 \times 10E-17$ moles of lipid-encapsulated TevCas9 per cell.

For in vivo cell transfection: To assemble the lipid-encapsulated TevCas9, a lipid nanoparticle is mixed with the TevCas9 in a 2000:1 molar ratio in phosphate buffered saline and incubated at room temperature for 10 minutes. The molar ratio of lipid-encapsulated TevCas9 per cell for in vivo transfections is to be determined.

Other Embodiments

The nuclease might contain different combinations of the I-TevI domain, linker domain, Cas9 domain or guide RNA as highlighted below.

Modifications of the I-TevI Domain: Other versions of the I-TevI nuclease domain might contain different combinations of mutations to alter the site targeted by the I-TevI domain or the activity of the I-TevI domain, including mutations that alter the sequence recognized by I-TevI, such as K26 and/or C39. Other versions of the nuclease might substitute the I-TevI domain with other GIY-YIG nuclease domains, such as I-Bmol, Eco29kI, etc. Other versions do not contain Met$^1$ as a result of processing when expressed in E. coli.

Modifications of the Linker Domain: The linker domain might comprise one more of the following to alter binding specificity or activity of TevCas9, including: a). The I-TevI linker domain comprising one or more mutations to amino acid T95, V117, K135, Q158 or N140; b). The linker might contain various combinations of the amino acids shown in SEQ ID NO: 9-12.

Modifications of the Cas9 Domain: Other versions of the Cas9 domain might contain the following: a). A version of the saCas9 domain comprising a D10E mutation (SEQ ID NO:14); b). A version of the saCas9 domain that nicks target DNA on one strand of the target DNA, for example the H557A mutation (SEQ ID NO: 17); c). A version of the saCas9 domain that binds target DNA but does not cleave it, for example mutations at both D10A and H557A mutations (SEQ ID NO: 18); d). A version of the previously described spCas9 EQR mutant comprising the mutations D1135E, R1335Q and T1337R combined with the D10E mutation (SEQ ID NO: 19); and e). A version of the previously described spCas9 EQR mutant comprising the mutations D1135E, R1335Q and T1337R combined with the D10E mutation and a mutation that nicks target DNA on one strand of the target DNA, for example the H840A mutation (SEQ ID NO: 20). Other versions of the saCas9 domain do not contain Met'.

Other versions might substitute other nucleases or DNA binding domains for the Cas9 domain, such as: a). Meganucleases such as the families LAGLIDADG, His-Cys Box, H—N—H, PD-(D/E)xK, Vsr-like, etc.; b). Zinc-finger nucleases; c). Other CRISPR proteins such as scCas9, fnCas9, cjCas9, Cpf1, Cas12a, Cas13a, Cas3, etc.; and d). Other DNA binding domains such as zinc-finger motifs, TALE activator domains, etc.

Modifications of the Guide RNA: a). Other versions of the guide RNA might target the same region of DNA in the CFTR gene or EGFR gene, but contain different sequences to account for genetic polymorphism in populations; b). Other versions of the guide RNA might target different sequences in the CFTR gene or EGFR gene; c). Other version of the guide RNA might target other sequences in a genome to retarget the nuclease to additional clinically relevant targets; d). Other versions of the guide RNA might contain bridged nucleic acids ("BNAs") to enhance target site specificity; and e). Other versions might contain a mixture of guide RNAs to target multiple sequences within the same gene.

Modifications of the Lipid Nanoparticles: a). Other versions of the lipid nanoparticle No. 1, 2 or 3 might have different ratios of each lipid component; b). Other versions of the lipid nanoparticle might have different mean diameters; c). Other versions of the lipid nanoparticle might include different cationic or neutral lipids; d). Other versions of the lipid nanoparticle might include peptides that target specific cell types; e). Other versions of the lipid nanoparticle might include compounds that bind DNA, such as GL67 ($N^4$—Cholesteryl-Spermine); f). the lipid nanoparticle might be lyophilized for enhanced stability; and g). the lipid nanoparticle might be resuspended in a solution other than phosphate buffered saline, such as sterile isotonic saline, water for injection, etc.

Modifications of the Composition of the donor DNA: a). Other version of the linear double-strand donor DNA might contain longer regions of single-strand DNA that is complementary to the target sequence; and b). Other versions of the circular double-strand DNA might contain other DNA sequences intended to increase the rate of homology-directed repair.

Variations to the method of assembling the lipid-encapsulated nuclease and transfecting cells: a). Other versions of the lipid-encapsulated nucleases might contain different molar ratios of lipid nanoparticle to nuclease; b). Media other than DMEM or phosphate buffered saline might be used for the incubation step; c). The nuclease and lipid nanoparticles might be incubated for less or more than 10 minutes; and d). Other molar amounts of nuclease per cell might be used in a transfection reaction.

Variations to the method to manufacture the nuclease: a). Other E. coli expression strains might be used, such as LS5218 (Escherichia coli Genetic Stock Center—Yale University, New Haven, Conn., United States) or BL21-DE3 (New England Biolabs, Ipswich, Mass., United States) b). Buffer 1 or 2 might contain different concentrations of imidazole, sodium chloride, sodium phosphate (dibasic), or tris hydrochloride and be buffered to a different pH; c). Other processing steps might be used, such as cation or anion exchange chromatography; d). The nuclease might be dialyzed into a solution other than phosphate buffered saline, such as sterile isotonic saline, water for injection, etc.; e). the nuclease might be lyophilized for enhanced stability; f). the guide RNA may be co-expressed from the pACYC-Duet1 expression vector (EMD Millipore, Burlington, Mass., United States). The DNA coding sequence of the guide RNA is synthesized (Integrated DNA Technology Inc., Coralville, Iowa, United States), digested with restrictions endonucleases and inserted into similarly-digested second expression site in the pACYC-Duet1 expression vector; and g). The guide RNA may be synthesized from double-strand DNA by transcribing the guide using the T7 RNA Polymerase HiScribe Kit (New England Biolabs #E2040S, Ipswich, Mass., United States) and purifying the guide using an RNA Cleanup Kit (New England Biolabs #T2030L, Ipswich, Mass., United States).

Testing

Example 1: A Method to Demonstrate Correction of CFTR Delta F508 and CFTR Protein Functionality in a Model Cell Line A culture of immortalized epithelial cells homozygous for the CFTR delta F508 mutation, such as the CuFi-1 cell line (ATCC® CRL-4013™, American Type Culture Collection, Manassas, Va., United States), is treated with a range of concentrations of lipid-encapsulated TevCas9 and donor DNA (Specific Biologics, Toronto, ON, Canada) in a pharmaceutical formulation targeted to the CFTR delta F508 mutation. An appropriate control cell line, such as NuLi-1 (ATCC® CRL-4011™, American Type Culture Collection, Manassas, Va., United States) immortalized epithelial cells homozygous for wild-type CFTR is also be used.

The proportion of cells with CFTR delta F508 corrected relative to uncorrected cells is measured by the T7 endonuclease I assay (EnGen® Mutation Detection Kit, New England Biolabs #E3321, Ipswich, Mass., United States), restriction endonuclease digestion (New England Biolabs, Ipswich, Mass., United States) of PCR-amplified target site, deep gene sequencing using an Illumina MiSeq system and barcoded primers flanking the target site (Illumina, San Diego, Calif., United States), or other suitable method. The effects of TevCas9 treatment in the control cell line (e.g. NuLi-1 (ATCC® CRL-4011™, American Type Culture Collection, Manassas, Va., United States) is measured. CFTR functionality is measured using short circuit current measurements in an Ussing Camber (Warner Instruments, Hamden, Conn., United States) in the presence of a chloride ion gradient in the treated CuFi-1 culture (ATCC® CRL-4013™, American Type Culture Collection, Manassas, Va., United States) versus mock-treated CuFi-1 culture (ATCC® CRL-4013™, American Type Culture Collection, Manassas, Va., United States). The effects of TevCas9 treatment in the control cell line (e.g. NuLi-1) is also measured.

To demonstrate disruption of the EGFR exon 19 deletion mutations(s) and EGFR expression and activity in a model cell line, a culture of immortalized epithelial cells expressing an EGFR exon 19 deletion mutation(s), such as the HCC827 cell line (ATCC® CRL-2868™, American Type Culture Collection, Manassas, Va., United States) is treated with a range of concentrations of lipid-encapsulated TevCas9 (Specific Biologics, Toronto, ON, Canada) in a pharmaceutical formulation of phosphate buffered saline, sterile isotonic saline or water for injection targeted to the EGFR exon 19 deletion. Appropriate control cell lines, such as NuLi-1 (ATCC® CRL-4011™, American Type Culture Collection, Manassas, Va.) or immortalized epithelial cell lines homozygous for wild-type EGFR, are used.

The proportion of cells with the EGFR exon 19 deletion disrupted relative to uncorrected cells is measured by the T7 endonuclease I assay (EnGen® Mutation Detection Kit, New England Biolabs #E3321, Ipswich, Mass., United States), restriction endonuclease digestion (New England Biolabs, Ipswich, Mass., United States) of PCR-amplified target site, deep gene sequencing using an Illumina MiSeq system and barcoded primers flanking the target site (Illumina, San Diego, Calif., United States), or other suitable method. The effects of TevCas9 treatment in the control cell line (e.g. NuLi-1 (ATCC® CRL-4011™, American Type Culture Collection, Manassas, Va., United States)) is also measured. EGFR protein expression and activity are measured using an enzyme-linked immunosorbent assay (ELISA) (Sigma, St. Louis, Mo., United States) that detects phosphorylated (i.e. activated), unphosphorylated and total EGFR protein in the treated HCC827 culture (ATCC® CRL-2868™, American Type Culture Collection, Manassas, Va., United States) versus mock-treated HCC827 culture. The effects of TevCas9 treatment in the control cell line (e.g. NuLi-1 (ATCC® CRL-4011™, American Type Culture Collection, Manassas, Va., United States)) is also measured.

Example 1: Animal Model Testing Planned to Show Efficacy and Determine Dose-Limiting Toxicity In an example method to demonstrate correction of CFTR delta F508 and/or Cystic Fibrosis symptoms with lipid-encapsulated TevCas9 treatment in an animal model (for example, mouse, rat, minipig or ferret), the lipid-encapsulated TevCas9 in a pharmaceutical formulation of phosphate buffered saline, sterile isotonic saline or water for injection targeted to the CFTR delta F508 is delivered directly to the lungs by either intubation or intranasal delivery. The procedure time is approximately 30-6000 seconds per treatment, depending on the animal model used.

In another method, the lipid-encapsulated TevCas9 in a pharmaceutical formulation targeted to the CFTR delta F508 is nebulized with a commercial nebulizer (Aeroneb®, AeroEclipse®, (Trudell Medical, London, ON, Canada)) or PARI-LC Plus®, (PARI USA, Midlothian, Va., United States)). The average size of the lipid nanoparticle of approximately 100 nM is confirmed post-nebulization by Dynamic Light Scattering (DLS) using a Zetasizer (Malvern Panalytical Ltd, Malvern, United Kingdom), or another suitable technique, known in the art. The composition and concentration of the lipid-encapsulated TevCas9 is confirmed post-nebulization using the MicroGram Lipid Assay Kit (ProFoldin, Hudson, Mass., United States) and the presence of an approximately 150 kDa band on a Coomassie-stained SDS-polyacrylamide gel. For measurement of the rate of gene correction, a representative ovine (minipig) animal model (Exemplar Genetics, Sioux City, Iowa, United States) that is homozygous for the CFTR delta F508 mutation is exposed through the mouth, nose or directly to the lungs with the lipid-encapsulated TevCas9 targeted to CFTR delta F508, as well as a suitable control. General maintenance of these animals includes breeding and farrowing; age-appropriate, bio-secure housing; sound nutrition; basic vaccinations and veterinary care; and documentation consistent with animal welfare guidelines. Maintenance of these animals specific to the CFTR delta F508 may include one of more of the following: surgery to address intestinal obstruction; pancreatic enzyme replacement therapy; vitamins and H2 blockers; and/or proton pump inhibitors to improve gastric acid control. The minipigs are treated with a range of concentrations of lipid-encapsulated TevCas9 that are predicted to be effective from the model cell line studies above for 2 days to 4 weeks for acute toxicity studies and up to 24 months for chronic toxicity studies.

The general health of the animal is monitored post-treatment to assess for any treatment-related adverse events, such as changes in behavior, weight, or food consumption; immune responses; changes to cardiovascular health; mortality, etc. Other efficacy measures post-treatment may include:
  I. Forced-expiration, such as forced expiratory volume (or other suitable method) in each animal post-treatment;
  II. Overall survival of each animal relative to the control;
  III. Other measures of lung function (for example, utilization of mechanical ventilator that can perform general lung function assessments); and
  IV. Measurements of the mutation in vivo through tissue sampling and mutation detection methods, such as by polymerase chain reaction.

After the treatment(s) with lipid-encapsulated TevCas9, the animals are sacrificed and the lung and tracheal tissue are harvested.

The proportion of cells with CFTR delta F508 corrected relative to uncorrected cells is measured by the T7 endonuclease I assay (EnGen® Mutation Detection Kit, New England Biolabs #E3321, Ipswich, Mass., United States), restriction endonuclease digestion (New England Biolabs, Ipswich, Mass., United States) of PCR-amplified target site, deep gene sequencing using an Illumina MiSeq system and barcoded primers flanking the target site (Illumina, San Diego, Calif., United States) or other suitable method.

In a method to demonstrate disruption of the EGFR exon 19 deletion mutation(s) and/or Non-small-cell lung cancer (NSCLC) symptoms with TevCas9 treatment in an animal model, the lipid-encapsulated TevCas9 targeted to the EGFR exon 19 deletion mutations in a pharmaceutical formulation of phosphate buffered saline, sterile isotonic saline or water for injection is delivered directly to the lungs through the mouth, nose or directly to the lungs. The procedure time is approximately 30-6000 seconds per treatment, depending on the animal model used.

In another method, the lipid-encapsulated TevCas9 targeted to the EGFR exon 19 deletion mutations in a pharmaceutical formulation is nebulized with a commercial nebulizer ((Aeroneb®, AeroEclipse®, (Trudell Medical, London, ON, Canada) or PARI-LC Plus®, (PART USA, Midlothian, Va., United States)). The average size of the lipid nanoparticle of approximately 100 nM is confirmed post-nebulization by Dynamic Light Scattering (DLS) using a Zetasizer (Malvern Panalytical Ltd, Malvern, United Kingdom), or another suitable technique, known in the art. The composition and concentration of the lipid-encapsulated TevCas9 nanoparticle is confirmed post-nebulization using the MicroGram Lipid Assay Kit (ProFoldin, Hudson, Mass., United States) and the presence of an approximately 150 kDa band on a Coomassie-stained SDS-polyacrylamide gel. For measurement of the rate of gene disruption, a representative murine (mouse) animal model that is homozygous for an EGFR exon 19 deletion mutation(s) is exposed through the nose, mouth or directly to the lungs with the lipid-encapsulated TevCas9 targeted to EGFR exon 19 deletion. The mice are treated with a range of concentrations of TevCas9 that are predicted to be effective from the model cell line studies for 2 days to 4 weeks for acute toxicity studies and up to 24 months for chronic toxicity studies.

The general health of the animal is monitored post-treatment to assess for any treatment-related adverse events, such as changes in behavior, weight, or food consumption; immune responses; changes to cardiovascular health; mortality, etc. Other efficacy measures post-treatment may include:
 I. Quantification of EGFR-activating protein through positron emission tomography (PET) with an EGFR mutant tracer;
 II. Overall survival of each animal relative to the control(s); and
 III. Measures of tumor formation/reduction in each animal over time.

Measurements of the mutation in vivo through tissue sampling and mutation detection methods, such as the Cobas® EGFR mutation test version 2 (Roche Diagnostics, Risch-Rotkreuz, Switzerland). After treatment with nebulized lipid-encapsulated TevCas9, the animals are sacrificed and the lung and tracheal tissue are harvested.

The proportion of cells with the EGFR exon 19 deletion mutation disrupted relative to undisrupted is measured by the T7 endonuclease I assay (EnGen® Mutation Detection Kit, New England Biolabs #E3321, Ipswich, Mass., United States), restriction endonuclease digestion (New England Biolabs, Ipswich, Mass., United States) of PCR-amplified target site, deep gene sequencing using an Illumina MiSeq system and barcoded primers flanking the target site (Illumina, San Diego, Calif., United States) or other suitable method. EGFR protein expression and activity in cells of the harvest tissues are measured using an enzyme-linked immunosorbent assay (ELISA) (Sigma, St. Louis, Mo., United States) that detects phosphorylated (i.e. activated), unphosphorylated and total EGFR protein. Determination of dose-limiting toxicity to enable first-in-human clinical studies is based on the predicted effective dose(s) from the animal model studies discussed above, a range of concentrations (in milligrams per kilogram body weight, for example) of lipid-encapsulated TevCas9 is nebulized and delivered to an appropriate animal model for toxicology studies, such as the cynomolgus monkey or other non-human primate. The general health of the animals is monitored for any treatment-related adverse events, such as changes in behavior, weight, or food consumption; immune responses; changes to cardiovascular health; mortality, etc. Other measures of efficacy may be measured in the studies, including those described above.

Therapeutic Effect

The novel chimeric nucleases of the instant invention have been intentionally designed to modify the DNA of lung epithelial cells to treat monogenetic diseases although they are capable of working in other cell types or in the cells of other organisms such as bacteria, yeast, insect, plant or other mammals in vivo or ex vivo to treat monogenetic or polygenetic and infectious diseases.

Example 1: A Method of Targeted Insertion or Replacement of all or a Portion of a DNA Sequence in the Genome of Human Cells FIG. 2A to 2E illustrate the mechanism of action of cellular uptake of the novel chimeric nuclease of the instant invention. As illustrated in FIG. 2A, a cell 20 or cells 20 are exposed to the novel lipid-encapsulated nuclease particles 21 containing the TevCas9 25 either by in vivo or ex vivo administration. As shown in FIG. 2B, the lipid-encapsulated nuclease particle 21 is endocytosed into the cell 20. The endosome 22 goes through a maturation process in the cytosol and is targeted for degradation (FIG. 2C). On certain occasions, the TevCas9 25 can escape the endosome 22 and enter the cytosol (FIG. 2D). In eukaryotic organisms, the nuclease (TevCas9) 25 is targeted to the nucleus 23 of the cell 20 through one or more nuclear-localization sequences ("NLS"). As depicted in FIG. 2E, through its nuclear localization sequence, TevCas9 25 can enter the nucleus 23 and when in the nucleus 23, the TevCas9 nuclease 25 binds to and cleaves 26 the target genomic DNA 24 sequence.

FIG. 3A to 3E illustrate the mechanism of the TevCas9 nuclease in cutting DNA. FIG. 3A is representation of the key features of TevCas9 bound to its target genomic DNA sequence 24 is shown prior to the cleavage reaction. The I-TevI domain 27 targets the I-TevI Target Sequence 29. The linker domain 30 joins the I-TevI domain 27 with the Cas9 domain 28 which targets the Cas9 Target Sequence 31. The gene mutation 32 is surrounded by or in close proximity to the I-TevI Target Sequence 29 and the Cas9 Target Sequence 31. As shown in FIG. 3B, the TevCas9 25 cleaves the target sequence leaving a deletion product 34 of a predictable size with non-complementary DNA ends 35, 36. FIG. 3C illustrates that in the presence of single-stranded donor DNA with homology arms 37, the cell 20 can insert the donor DNA 37 sequence near the cut sites through the homology-directed repair (HDR) pathway 38. FIG. 3D illustrates that in the presence of donor DNA 39 with compatible DNA ends to those cleaved by TevCas9 25, the cell 20 can insert the donor DNA sequence 39 between the cut sites through directed-ligation using the non-homologous end joining (NHEJ) pathway 40. In the absence of donor DNA, the cell 20 can join the DNA ends through the NHEJ pathway 40 (FIG. 3E).

Example 2: The Treatment of Cystic Fibrosis

For the treatment of cystic fibrosis, the exogenous donor DNA contains a DNA sequence, which repairs the CFTR delta F508 mutation involving a method of targeted deletion of a defined length of a DNA sequence in human somatic cells to stimulate homology-directed repair using exogenous donor DNA as a template (FIG. 3C).

Example 3: The Treatment of Non-Small Cell Lung Cancer

For the application of treating non-small cell lung cancer, a version of the Cas9 domain which cuts only one strand of DNA (D10A or H557A mutation) or a nuclease deficient version (the D10A+H557A mutations) is used and the sequences targeted are EGFR exon 19 deletion mutations (SEQ ID NOS: 2-4). In this application, however, the nuclease does not contain exogenous donor DNA. In the absence of exogenous donor DNA, the cell can remove the DNA sequence between the two sites targeted by the nuclease by non-homologous end joining (FIG. 3E).

Alternatively, the inhalation route is a fast and effective way of delivering medication locally to the lungs and for the systemic administration of certain agents. Inhalation drug therapy is used extensively to treat respiratory conditions such as asthma and Chronic Obstructive Pulmonary Disease (COPD). Research is ongoing to develop inhalation systems to treat cystic fibrosis.

The examples which follow are intended in no way to limit the scope of the disclosure but are provided to illustrate how to prepare and use compounds disclosed herein. Many other embodiments of this disclosure will be apparent to one skilled in the art.

A nebulizer is a device that delivers medication to the lungs in the form of an aerosolized vapor. Nebulizers are commonly used to treat respiratory diseases such as asthma and COPD, for example, the nebulization of corticosteroids, although nebulization has also been used for the treatment and prevention of lung infections, such as ARIKAYCE® (Insmed Incorporated, Bridgewater, N.J., United States).

The nebulizer may require some procedure to prepare the liquid for nebulization. The medication is commonly held in liquid form in a cup inside the nebulizer chamber. Once loaded, the device is switched on which generates compressed air to convert the liquid into a vapor in the nebulization chamber. The patient puts the mouthpiece of the nebulization chamber into their mouth and takes a sharp, deep inhalation, holding their breath for 5-10 seconds to ensure the medication reaches the lower parts of the lung. There are a variety of such devices. Many modern nebulizers are breath-actuated and rely on the force of patient inhalation to entrain the aerosolized liquid from the device and thus ensure the medication is delivered only to the patient and not to the surrounding environment. This also ensures consistency of delivering a full dose of the medication to the patient.

The use of nebulizers is well known and nebulizers are commercially available from several sources, such as Aeroneb®, AeroEclipse®, (Trudell Medical, London, ON, Canada) or PARI-LC Plus®, (PART USA, Midlothian, Va., United States). In an example of the present invention, a nebulizer is utilized for delivery of the lipid-encapsulated novel chimeric nuclease comprising a modified I-TevI nuclease domain, a linker, and a modified RNA-guided nuclease *Staphylococcus aureus* Cas9 of the instant application to the lung epithelial tissue. A sterile liquid version of the therapeutic of interest is loaded into the nebulization chamber and is subsequently aerosolized and is inhaled by the patient into the lung via deep breaths.

Some of the advantages of using a nebulizer versus oral or intravenous administration are: less drug could be required compared to oral or intravenous administration, onset of action can be more rapid via inhalation compared to the oral route, adverse effects are potentially less severe due to local delivery of the medication to the lung tissue where the disease manifests itself, inhaled drug therapy is painless and relatively comfortable for the patient which encourages compliance.

No non-invasive route of delivery provides the speed of action that an inhaled drug can provide. One of the advantages of inhaled drugs is that they are more rapidly absorbed than subcutaneously injected molecules and provides a more immediate physiological response. Small or large molecules, particularly hydrophobic molecules, can be absorbed within seconds after inhalation and can thus be used to treat a wide variety of symptoms that come on suddenly or need long term administration. Pain, panic, anxiety, nausea, cardiovascular crises, bronchoconstriction, sleep induction, spasms, Parkinson's lock-up, and hot flashes are some of the rapid-onset conditions that are addressable with inhaled medicines.

Most protein-based drug products have some water solubility and are rapidly and efficiently absorbed from the lungs. Those that are more hydrophobic are absorbed even more rapidly within seconds to a few minutes. Those that are more hydrophilic are absorbed within minutes to tens of minutes. In one example of the present invention, one vial is aseptically filled with a therapeutic dose of the lipid nanoparticle which is hydrophobic and another vial is aseptically filled with a therapeutic dose of a chimeric nuclease comprising a modified I-TevI nuclease domain, a linker and a modified RNA-guided nuclease *Staphylococcus aureus* Cas9 which is water soluble and hydrophilic, for delivery to the lungs of a therapeutic dose. The dose can range from 1 to 1000 milligrams of each of the lipid nanoparticle and chimeric nuclease with about 5 to 200 milligrams being preferred. The claimed lipid-encapsulated chimeric nuclease comprising a modified I-TevI nuclease domain, a linker, and a modified RNA-guided nuclease *Staphylococcus aureus* Cas9 can be absorbed in the cells of the lungs within a few hours and complete cleavage on DNA substrates in vitro has been observed within 2 hours. Other nebulized therapies have been delivered daily. Nebulized administration of the lipid-encapsulated chimeric nuclease, therefore, can be daily or more infrequently depending on its efficacy on a per patient basis. The chimeric nucleases are manufactured by BioVectra Corporation (Charlottetown, PE, Canada) and the vials are aseptically filled by Dalton Pharma Services (Mississauga; ON, Canada). The lipid nanoparticles are manufactured and the vials are aseptically filled by Transferra Nanosciences Inc. (Burnaby, BC, Canada).

The dosage of any disclosed compositions will vary depending on the symptoms, age and body weight of the patient, the nature and severity of the disorder to be treated or prevented, the route of administration, and the form of the subject composition. Any of the subject formulations may be administered in a single dose or in divided doses. Dosages for the compositions may be readily determined by techniques known to those of skill in the art or as taught herein.

In certain embodiments, the dosage of the subject compounds will generally be in the range of about 1 to 1000 milligrams depending on the body weight of the patient, specifically in the range of about 5 to 200 milligrams.

An effective dose or amount, and any possible effects on the timing of administration of the formulation, may need to be identified for any particular composition of the disclosure. This may be accomplished by routine experiment as described herein, using one or more groups of animals (preferably at least 5 animals per group), or in human trials if appropriate. The effectiveness of any subject composition and method of treatment or prevention may be assessed by administering the composition and assessing the effect of the administration by measuring one or more applicable indices and comparing the post-treatment values of these indices to the values of the same indices prior to treatment.

The precise time of administration and amount of any particular subject composition that will yield the most effective treatment in a given patient will depend upon the activity, pharmacokinetics, and bioavailability of a subject composition, physiological condition of the patient (including age, sex, disease type and stage, general physical condition, responsiveness to a given dosage and type of medication), route of administration, and the like. The guidelines presented herein may be used to optimize the treatment, e.g., determining the optimum time and/or amount of administration, which will require no more than routine experimentation consisting of monitoring the subject and adjusting the dosage and/or timing.

While the subject is being treated, the health of the patient may be monitored by measuring one or more of the relevant indices at predetermined times during the treatment period. Treatment, including composition, amounts, times of administration and formulation, may be optimized according to the results of such monitoring. The patient may be periodically re-evaluated to determine the extent of improvement by measuring the same parameters. Adjustments to the amount(s) of subject composition administered and possibly to the time of administration may be made based on these re-evaluations.

Treatment may be initiated with smaller dosages which are less than the optimum dose of the compound. Thereafter, the dosage may be increased by small increments until the optimum therapeutic effect is attained.

The use of the subject compositions may reduce the required dosage for any individual agent contained in the compositions because the onset and duration of effect of the different agents may be complimentary.

Therapeutic efficacy of subject compositions may be determined by standard pharmaceutical procedures in cell cultures or experimental animals, e.g., for determining the $LD_{50}$ and the $ED_{50}$.

The data obtained from the cell culture assays and animal studies may be used in formulating a range of dosage for use in humans. The dosage of any subject composition lies preferably within a range of concentrations that include the $ED_{50}$ with little or no toxicity. The dosage may vary within this range depending upon the dosage form employed and the route of administration utilized. For compositions of the disclosure, the therapeutically effective dose may be estimated initially from cell culture assays.

Formulations

Pharmaceutical compositions of the disclosure may be administered by various means, depending on their intended use, as is well known in the art. For example, compositions of the disclosure are to be administered through nebulization. Alternatively, formulations disclosed herein may be administered intravenously, subcutaneously, or intramuscularly. These formulations may be prepared by conventional means, and, if desired, the compositions may be mixed with any conventional additive, such as an excipient, a solubilizing agent, a suspension aid, an emulsifying agent, or preservative agent. The disclosed excipients may serve more than one function. For example, a solubilizing agent may also be a suspension aid, an emulsifier, a preservative, and the like.

The formulations may conveniently be presented in unit dosage form and may be prepared by any methods well known in the art of pharmacy. The amount of a composition that may be combined with a carrier material to produce a single dose vary depending upon the subject being treated, and the particular mode of administration.

Methods of preparing these formulations include the step of bringing into association compositions of the disclosure with the carrier and, optionally, one or more accessory ingredients. In general, the formulations are prepared by uniformly and intimately bringing into association agents with liquid carriers.

It will be appreciated that a disclosed composition may include lyophilized or freeze-dried compounds disclosed herein. For example, disclosed herein are compositions that disclosed compounds crystalline and/or amorphous powder forms. Such forms may be reconstituted for use as e.g., an aqueous composition.

Liquid dosage forms for injection include pharmaceutically acceptable solutions, emulsions, microemulsions, solutions and suspensions. In addition to the subject composition, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, glycerol, tetrahydrofuryl alcohol, and fatty acid esters of sorbitan, cyclodextrins, albumin, hyaluronic acid, chitosan and mixtures thereof. Polyethylene glycol (PEG) may be used to obtain desirable properties of solubility, stability, half-life, and other pharmaceutically advantageous properties. Representative examples of stabilizing components include polysorbate 80, L-arginine, polyvinylpyrrolidone, trehalose, and combinations thereof. Other excipients that may be employed, such as solution binders or anti-oxidants include, but are not limited to, butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, sucrose, talc, titanium dioxide, vitamin A, vitamin E (alpha-tocopherol), vitamin C and xylitol.

Ordinarily, an aqueous aerosol is made by formulating an aqueous solution or suspension of a subject composition together with conventional pharmaceutically acceptable carriers and stabilizers. The carriers and stabilizers vary with the requirements of the particular subject composition, but typically include non-ionic surfactants (Tweens, pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

It should be noted that excipients given as examples may have more than one function. For example, a solubilizing agent may also be a suspension aid, an emulsifier, a preservative and the like.

Examples of suitable aqueous and non-aqueous carriers which may be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate and cyclodextrins. Proper fluidity may be maintained, for example, by the use of coating materials, such as lecithin, by the maintenance of the required particle size in the case of dispersions, and by the use of surfactants.

The compositions of the present invention typically are ready to administer, aqueous solutions which are sterile, storage-stable, and pharmaceutically acceptable without the need for reconstitution prior to administration. The compositions of the present invention are suitable for administration to a subject which means that they are pharmaceutically acceptable, non-toxic, do not contain any components which would adversely affect the biological effects of the chimeric nuclease, and have the pH close to that of the physiological condition which avoids inhalation and/or injection site reactions. The compositions of the present invention do not, for example, comprise any cells.

The compositions are typically stored in a sealed container, vial or cartridge which is typically suitable for long term storage. "Suitable for long-term storage" means that the vial, container or cartridge does not allow for the escape of components of the compositions of the present invention or the ingress of external components, such as, microorganisms when kept for at least 3 months at 25° C.

The compositions of the present invention are preferably administered by nebulization, typically breath-actuated nebulization.

The compositions of the present invention can also be administered by injection as described herein.

The compositions of the present invention may be administered alone or in combination with an additional therapeutic agent, such as an anti-viral, an anti-microbial, a chemotherapeutic and an immunotherapy.

Vials, as used herein, can also comprise two containers one of which contains the chimeric nuclease or lipid particle, as described herein, in a lyophilized powder, as described below, and the second container contains a liquid for reconstitution of the lyophilized powder. The contents of the two containers can be mixed prior to administration.

As discussed above the compositions of the present invention can be administered by nebulization. Suitable volumes of the compositions of the present invention for nebulization include about 0.5 to about 1 ml, about 1 to about 2 ml, about 2 to about 10 ml, or about 10 to about 20 ml.

In the compositions of the present invention the concentration of the chimeric nuclease is from about 0.1 mg/ml to about 10.0 mg/ml, from about 10.0 mg/ml to about 100.0 mg/ml, from about 30.0 mg/ml to about 300.0 mg/ml, from about 500 mg/ml to about 2000 mg/ml and about 2.0 mg/ml.

In the compositions of the present invention the concentration of the lipid nanoparticle is from about 0.1 mg/ml to about 10.0 mg/ml, from about 10.0 mg/ml to about 100.0 mg/ml, from about 30.0 mg/ml to about 300.0 mg/ml, from about 500 mg/ml to about 2000 mg/ml and about 2.0 mg/ml.

We claim:

1. A nuclease comprising a modified *Staphylococcus aureus* Cas9 comprising the sequence of SEQ ID NO: 14.

2. The nuclease of claim 1, wherein the modified *Staphylococcus aureus* Cas9 further comprises a histidine to alanine substitution at an amino acid corresponding to position 557 of SEQ ID NO: 13.

3. The nuclease of claim 1, further comprising an Enterobacteria Phage T4 I-TevI nuclease domain.

4. The nuclease of claim 3, wherein the I-TevI nuclease domain comprises the amino acid sequence set forth in SEQ ID NO: 6.

5. The nuclease of claim 4, wherein the I-TevI nuclease domain comprises a substitution or deletion of the methionine at position 1 of SEQ. ID NO: 6.

6. The nuclease of claim 1, further comprising a linker coupling the modified *Staphylococcus aureus* Cas9 and the I-TevI nuclease domain.

7. The nuclease of claim 6, wherein the linker comprises an amino acid sequence set forth in any one or more of SEQ ID NO: 7 to SEQ ID NO 12.

8. The nuclease of claim 1, bound to a guide RNA.

9. The nuclease of claim 8, wherein the guide RNA comprises one or more bridged nucleic acids.

10. A chimeric nuclease comprising an I-TevI nuclease domain, a linker, a *Staphylococcus aureus* Cas9, and a guide RNA, wherein the *Staphylococcus aureus* Cas9 comprises the sequence of SEQ ID NO: 14.

11. The chimeric nuclease of claim 10, wherein the *Staphylococcus aureus* Cas9 comprises an aspartic acid to glutamic acid substitution at an amino acid corresponding to position 10 of SEQ ID NO: 13.

12. The chimeric nuclease of claim 10, wherein the I-TevI nuclease domain comprises the amino acid sequence set forth in SEQ ID NO: 6.

13. The chimeric nuclease of claim 12, wherein the I-TevI nuclease domain comprises a substitution or deletion of the methionine at position 1 of SEQ NO: 6.

14. The chimeric nuclease of claim 10, wherein the linker comprises an amino acid sequence set forth in any one or more of SEQ ID NO: 7 to SEQ ID NO 12.

15. A formulation comprising the chimeric nuclease of claim 11 and a lipid nanoparticle.

16. A method to genetically modify the genome of a cell, the method comprising: contacting the cell with the chimeric nuclease of claim 10.

17. A nucleic acid encoding the nuclease of claim 1.

18. A nucleic acid encoding the chimeric nuclease of claim 10.

* * * * *

SEQUENCE LISTING

```
Sequence total quantity: 20
SEQ ID NO: 1            moltype = DNA  length = 4440
FEATURE                 Location/Qualifiers
source                  1..4440
                        mol_type = other DNA
                        organism = Homo sapiens
SEQUENCE: 1
atgcagaggt cgcctctgga aaaggccagc gttgtctcca aacttttttt cagctggacc    60
agaccaattt tgaggaaagg atacagacag cgcctggaat tgtcagacat ataccaaatc   120
ccttctgttg attctgctga caatctatct gaaaaattgg aaagagaatg ggatagagag   180
ctggcttcaa agaaaaatcc taaactcatt aatgcccttc ggcgatgttt tttctggaga   240
tttatgttct atggaatctt tttatattta ggggaagtca ccaaagcagt acagcctctc   300
ttactgggaa gaatcatagc ttcctatgac ccggataaca aggaggaacg ctctatcgcg   360
atttatctag gcataggctt atgccttctc tttattgtga ggacactgct cctacaccca   420
gccatttttg gccttcatca cattggaatg cagatgagaa tagctatgtt tagtttgatt   480
tataagaaga ctttaaagct gtcaagccgt gttctagata aaataagtat tggacaactt   540
gttagtctcc tttccaacaa cctgaacaaa tttgatgaag gacttgcatt ggcacatttc   600
gtgtggatcg ctcctttgca agtggcactc ctcatggggc taatctggga gttgttacag   660
gcgtctgcct tctgtggact tggtttcctg atagtccttg cccttttttca ggctgggcta   720
gggagaatga tgatgaagta cagagatcag agagctggga agatcagtga aagacttgtg   780
attacctcag aaatgattga aaatatccaa tctgttaagg catactgctg ggaagaagca   840
atggaaaaaa tgattgaaaa cttaagacaa acagaactga aactgactcg gaaggcagcc   900
tatgtgagat acttcaatag ctcagccttc ttcttctcag ggttctttgt ggtgttttta   960
tctgtgcttc cctatgcact aatcaaagga atcatcctcc ggaaaatatt caccaccatc  1020
tcattctgca ttgttctgcg catggcggtc actcggcaat ttcccctggc tgtacaaaca  1080
tggtatgact ctcttggagc aataaacaaa atacaggatt tcttacaaaa gcaagaatat  1140
aagacattgg aatataactt aacgactaca gaagtagtga tggagaatgt aacagccttc  1200
tgggaggagg gatttgggga attatttgag aaagcaaaac aaaacaataa caatagaaaa  1260
acttctaatg gtgatgacag cctcttcttc agtaatttct cacttcttgg tactcctgtc  1320
```

```
ctgaaagata ttaatttcaa gatagaaaga ggacagttgt tggcggttgc tggatccact   1380
ggagcaggca agacttcact tctaatggtg attatgggag aactggagcc ttcagagggt   1440
aaaattaagc acagtggaag aatttcattc tgttctcagt tttcctggat tatgcctggc   1500
accattaaag aaaatatcat tggtgtttcc tatgatgaat atagatacag aagcgtcatc   1560
aaagcatgcc aactagaaga ggacatctcc aagtttgcag agaaagacaa tatagttctt   1620
ggagaaggtg gaatcacact gagtggaggt caacgagcaa gaatttcttt agcaagagca   1680
gtatacaaag atgctgattt gtatttatta gactctcctt ttggatacct agatgtttta   1740
acagaaaaag aaatatttga aagctgtgtc tgtaaactga tggctaacaa aactaggatt   1800
ttggtcactt ctaaaatgga acatttaaag aaagctgaaca aaatattaat tttgcatgaa   1860
ggtagcagct attttatgg gacatttca gaactccaaa atctacagcc agactttagc    1920
tcaaaactca tgggatgtga ttctttcgac caatttagtg cagaaagaag aaattcaatc   1980
ctaactgaga cccttacaccg tttctcatta gaaggagatg ctcctgtctc ctggacagaa   2040
acaaaaaaac aatcttttaa acagactgga gagtttgggg aaaaaaggaa gaattctatt   2100
ctcaatccaa tcaactctat acgaaaattt tccattgtgc aaaagactcc cttacaaatg   2160
aatggcatcg aagaggattc tgatgagcct ttagagagaa ggctgtcctt agtaccagat   2220
tctgagcagg gagaggcgat actgcctcgc atcagcgtga tcagcactgg ccccacgctt   2280
caggcacgaa ggaggcagtc tgtcctgaac ctgatgacac actcagttaa ccaaggtcag   2340
aacattcacc gaaagacaac agcatccaca cgaaaagtgt cactggcccc tcaggcaaac   2400
ttgactgaac tggatatata ttcaagaagg ttatctcaag aaactggctt ggaaataagt   2460
gaagaaatta acgaagaaga cttaaaggag tgctttttg atgatatgga gagcatacca   2520
gcagtgacta catggaacac ataccttcga tatattactg tccacaagag cttaattttt   2580
gtgctaattt ggtgcttagt aattttttctg gcagaggtgg ctgcttcttt ggttgtgctg   2640
tggctccttg gaaacactcc tcttcaagac aaagggaata gtactcatag tagaaataac   2700
agctatgcag tgattatcac cagcaccagt tcgtattatg tgttttacat ttacgtggga   2760
gtagccgaca ctttgcttgc tatgggattc ttcagaggtc taccactggt gcatactcta   2820
atcacagtgt cgaaaatttt acaccacaaa atgttacatt ctgttcttca agcacctatg   2880
tcaaccctca acacgttgaa agcaggtggg attcttaata gattctccaa agatatagca   2940
attttggatg accttctgcc tcttaccata tttgacttca tccagttgtt attaattgtg   3000
attggagcta tagcagttgt cgcagttta caaccctaca tctttgttgc aacagtgcca   3060
gtgatagtgg ctttttatat gttgagagca tattccctcc aaacctcaca gcaactcaaa   3120
caactggaat ctgaaggcag gagtccaatt ttcactcatc ttgttacaag cttaaaagga   3180
ctatggacac ttcgtgcctt cggacggcag ccttactttg aaactctgtt ccacaaagct   3240
ctgaatttac atactgccaa ctggttcttg tacctgtcaa cactgcgctg gttccaaatg   3300
agaatagaaa tgattttgt catcttcttc attgctgtta ccttcatttc cattttaaca   3360
acaggagaag gagaaggaag agttggtatt atcctgactt tagccatgaa tatcatgagt   3420
acattgcagt gggctgtaaa ctccagcata gatgtggata gcttgatgcg atctgtgagc   3480
cgagtcttta gttcattga catgccaaca gaaggtaaac ctaccaagtc aaccaaacca   3540
tacaagaatg gccaactctc gaaagttatg attattgaga attcacacgt gaagaaagat   3600
gacatctggc cctcagggg ccaaatgact gtcaaagatc tcacagcaaa atacacagaa   3660
ggtgaaaatg ccatattaga gaacattcc ttctcaataa gtcctggcca gagggtgggc   3720
ctcttgggaa gaactggatc agggaagagt actttgttat cagctttttt gagactactg   3780
aacactgaag gagaaatcca gatcgatggt gtgtcttggg attcaataac tttgcaacag   3840
tggaggaaag cctttggagt gataccacag aaagtatta ttttttctgg aacattttga    3900
aaaaacttgg atccctatga acagtggagt gatcaagaaa tatggaaagt tgcagatgag   3960
gttgggctca gatctgtgat agaacagttt cctgggaagc ttgactttgt ccttgtggat   4020
gggggctgtg tcctaagcca tggccacaag cagttgatgt gcttggctag atctgttctc   4080
agtaaggcga agatctgct gcttgatgaa cccagtgctc atttggatcc agtaacatac   4140
caaataatta aagaactct aaaacaagca tttgctgatt gcacagtaat tctctgtgaa   4200
cacaggatag aagcaatgct ggaatgccaa caatttttgg tcatagaaga gaacaaagtg   4260
cggcagtacg attccatcca gaaactgctg aacgagagga gcctcttccg gcaagccatc   4320
agcccctccg cagggtgaa gctctttccc caccggaact caagcaagtg caagtctaag   4380
ccccagattg ctgctctgaa agaggagaca gaagaagagg tgcaagatac aaggctttag   4440
```

SEQ ID NO: 2          moltype = DNA   length = 3261
FEATURE                Location/Qualifiers
source                 1..3261
                        mol_type = other DNA
                        organism = Homo sapiens
SEQUENCE: 2

```
atgcgaccct ccgggacggc cggggcagcg ctcctggcgc tgctggctgc gctctgcccg   60
gcgagtcggg ctctggagga aaagaaagtt tgccaaggca cgagtaacaa gctcacgcag   120
ttgggcactt ttgaagatca ttttctcagc ctccagagga tgttcaataa ctgtgaggtg   180
gtccttggga atttggaaat tacctatgtg cagaggaatt atgatctttc cttcttaaag   240
accatccagg aggtggctgg ttatgtcctc attgccctca acacagtgga gcgaattcct   300
ttggaaaacc tgcagatcat cagaggaaat atgtactacg aaaattccta tgccttagca   360
gtcttatcta actatgatgc aaataaaacc ggactgaagg agctgccat gagaaattta   420
cagggacaaa agtgtgatcc aagctgtccc aatgggagct gctgggggtgc aggagaggag   480
aactgccaga aactgaccaa aatcatctgt gcccagcagt gctccgggcg ctgccgtggc   540
aagtccccca gtgactgctg ccacaaccag tgtgctgcag cccccggaga   600
agcgactgcc tggtctgccg caaattccga gacgaagcca cgtgcaagga cacctgcccc   660
ccactcatgc tctacaaccc caccacgtac cagatggatg tgaaccccga gggcaaatac   720
agctttggtg ccacctgcgt gaagaagtgt ccccgtaatt atgtggtgac agatcacggc   780
tcgtgcgtcc gagcctgtgg ggccgacagc tatgagatgg aggaagacgg cgtccgcaag   840
tgtaagaagt gcgaagggcc ttgccgcaaa gtgtgtaacg gtataggttt tggtgaattt   900
aaagactcac tctccataaa tgctacgaat attaaacact tcaaaaactg cacctccatc   960
agtggcgatc tccacatcct gccggtggca tttaggggtg actccttcac acatactcct   1020
cctctgatc cacaggaact ggatattctg aaaaccgtaa aggaaatcac agggttttg    1080
ctgattcagg cttggcctga aaacaggacg gacctccatg cctttgagaa cctagaaatc   1140
atacgcggca ggaccaagca acatggtcag ttttctcttg cagtcgtcag cctgaacata   1200
```

```
acatccttgg gattacgctc cctcaaggag ataagtgatg gagatgtgat aatttcagga   1260
aacaaaaatt tgtgctatgc aaatacaata aactggaaaa aactgtttgg gacctccggt   1320
cagaaaacca aaattataag caacagaggt gaaaacagct gcaaggccac aggccaggtc   1380
tgccatgcct tgtgctcccc cgagggctgc tggggcccgg agcccaggga ctgcgtctct   1440
tgccggaatg tcagccgagg cagggaatgc gtggacaagt gcaaccttct ggagggtgag   1500
ccaagggagt ttgtggagaa ctctgagtgc atacagtgcc acccagagtg cctgcctcag   1560
gccatgaaca tcacctgcac aggacgggga ccagacaact gtatccagtg tgcccactac   1620
attgacggcc cccactgcgt caagacctgc ccggcaggag tcatgggaga aaacaacacc   1680
ctggtctgga agtacgcaga cgccggccat gtgtgccacc tgtgccatcc aaactgcacc   1740
tacggatgca ctgggccagg tcttgaaggc tgtccaacga atgggcctaa gatcccgtcc   1800
atcgccactg ggatggtggg ggccctcctc ttgctgctgg tggtggccct ggggatcggc   1860
ctcttcatgc gaaggcgcca catcgttcgg aagcgcacgc tgcggaggct gctgcaggag   1920
agggagcttg tggagcctct tacacccagt ggagaagctc ccaaccaagc tctccttgagg  1980
atcttgaagg aaactgaatt caaaaagatc aaagtgctgg gctccggtgc gttcggcacg   2040
gtgtataagg gactctggat cccagaaggt gagaaagtta aaattcccgt cgctatcaaa   2100
acatctccga aagccaacaa ggaaatcctc gatgaagcct acgtgatggc cagcgtggac   2160
aaccccacg tgtgccgcct gctgggcatc tgcctcacct ccaccgtgca gctcatcacg   2220
cagctcatgc ccttcggctg cctcctggac tatgtccgga aacacaaaga caatattggc   2280
tcccagtacc tgctcaactg gtgtgtgcag atcgcaaagg gcatgaacta cttggaggac   2340
cgtcgcttgg tgcaccgcga cctggcagcc aggaacgtac tggtgaaaac accgcagcat   2400
gtcaagatca cagattttgg gctggccaaa ctgctgggtg cggaagagaa agaataccat   2460
gcagaaggag gcaaagtgcc tatcaagtgg atggcattgg aatcaatttt acacagaatc   2520
tatcccacc agagtgatgt ctggagctac ggggtgaccg tttgggagtt gatgaccttt   2580
ggatccaagc catatgacgg aatccctgcc agcgagatct cctccatcct ggagaaagga   2640
gaacgcctcc ctcagccacc catatgtacc atcgatgtct acatgatcat ggtcaagtgc   2700
tggatgatag acgcagatag tcgcccaaag ttccgtgagt tgatcatcga attctccaaa   2760
atggcccgag accccagcg ctaccttgtc attcaggagg atgaaagaat gcatttgcca   2820
agtcctacag actccaactt ctaccgtgcc ctgatggatg aagaagacat ggacgacgtg   2880
gtggatgccg acgagtacct catcccacag cagggcttct tcagcagccc ctccacgtca   2940
cggactcctc tcctgagctc tctgagtgca accagcaaca attccaccgt ggcttgcatt   3000
gatagaaatg ggctgcaaag ctgtcccatc aaggaagaca gcttcttgca gcgatacagc   3060
tcagacccca caggcgcctt gactgaggac agcatagacg acaccttcct cccagtgcct   3120
ggtgagtggc ttgtctggaa acagtcctgc tcctcaacct cctcgaccca ctcagcagca   3180
gccagtctcc agtgtccaag ccaggtgctc cctccagcat ctccagaggg ggaaacagtg   3240
gcagatttgc agacacagtg a                                             3261
```

SEQ ID NO: 3          moltype = DNA   length = 3260
FEATURE               Location/Qualifiers
source                1..3260
                      mol_type = other DNA
                      organism = Homo sapiens
SEQUENCE: 3
```
atgcgaccct ccgggacggc cggggcagcg ctcctggcgc tgctggctgc gctctgcccg   60
gcgagtcggg ctctggagga aagaaagtt tgccaaggca cgagtaacaa gctcacgcag   120
ttgggcactt ttgaagatca tttttctcagc ctccagagga tgttcaataa ctgtgaggtg   180
gtccttggga atttggaaat tacctatgtg cagaggaatt atgatctttc cttcttaaag   240
accatccagg aggtggctgg ttatgtcctc attgccctca cacagtggga gcgaattcct   300
ttggaaaacc tgcagatcat cagaggaaat atgtactacg aaaattccta tgccttagca   360
gtcttatcta actatgatgc aaataaaacc ggactgaagg agctgccat gagaaattta   420
cagggacaaa agtgtgatcc aagctgtccc aatgggagct gctggggtgc aggagaggag   480
aactgccaa aactgaccaa aatcatctgt gcccagcagt gctccgggcg ctgccgtggc   540
aagtcccca gtgactgctg ccacaaccag tgtgctgcag gctgcacagg ccccgggag   600
agcgactgcc tggtctgccg caaattccga gacgaagcca cgtgcaagga cacctgcccc   660
ccactcatgc tctacaaccc caccacgtac cagatgatgt gaaccccga gggcaaatac   720
agctttggtg ccacctgcgt gaagaagtgt ccccgtaatt atgtggtgac agatcacggc   780
tcgtgcgtcc agcctgtgg ggccgacagc tatgagatgg aggaagacgg cgtccgcaag   840
tgtaagaagt gcgaagggcc ttgccgcaaa gtgtgtaacg gaataggtat tggtgaattt   900
aaagactcac tctccataaa tgctacgaat attaaacact tcaaaaactg cacctccatc   960
agtgcgatc tcccacatcct gccggtgca tttaggggtg actccttcac acatactcct  1020
cctctggatc cacaggaact ggatattctg aaaaccgtaa aggaaatcac agggtttttg  1080
ctgattcagg cttggcctga aaacaggacg gacctccatg cctttgagaa cctagaaatc  1140
atacgcggca ggaccaagca acatggtcag ttttctcttg cagtcgtcag cctgaacata  1200
acatccttgg gattacgctc cctcaaggag ataagtgatg gagatgtgat aatttcagga  1260
aacaaaaatt tgtgctatgc aaatacaata aactggaaaa aactgtttgg gacctccggt  1320
cagaaaacca aaattataag caacagaggt gaaaacagct gcaaggccac aggccaggtc  1380
tgccatgcct tgtgctcccc cgagggctgc tggggcccgg agcccaggga ctgcgtctct  1440
tgccggaatg tcagccgagg cagggaatgc gtggacaagt gcaaccttct ggagggtgag  1500
ccaagggagt ttgtggagaa ctctgagtgc atacagtgcc acccagagtg cctgcctcag  1560
gccatgaaca tcacctgcac aggacgggga ccagacaact gtatccagtg tgcccactac  1620
attgacggcc cccactgcgt caagacctgc ccggcaggag tcatgggaga aaacaacacc  1680
ctggtctgga agtacgcaga cgccggccat gtgtgccacc tgtgccatcc aaactgcacc  1740
tacggatgca ctgggccagg tcttgaaggc tgtccaacga atgggcctaa gatcccgtcc  1800
atcgccactg ggatggtggg ggccctcctc ttgctgctgg tggtggccct ggggatcggc  1860
ctcttcatgc gaaggcgcca catcgttcgg aagcgcacgc tgcggaggct gctgcaggag  1920
agggagcttg tggagcctct tacacccagt ggagaagctc ccaaccaagc tctccttgagg 1980
atcttgaagg aaactgaatt caaaaagatc aaagtgctgg gctccggtgc gttcggcacg  2040
gtgtataagg gactctggat cccagaaggt gagaaagtta aaattcccgt cgctatcaag  2100
acatctccga aagccaacaa ggaaatcctc gatgagccta cgtgatggcc agcgtggaca  2160
accccccacg tgtgccgcct gctgggcatc tgcctcacct caccgtgcag ctcatcacgc  2220
```

```
agctcatgcc cttcggctgc ctcctggact atgtccggga acacaaagac aatattggct   2280
cccagtacct gctcaactgg tgtgtgcaga tcgcaagggg catgaactac ttggaggacc   2340
gtcgcttggt gcaccgcgac ctggcagcca ggaacgtact ggtgaaaaca ccgcagcatg   2400
tcaagatcac agattttggg ctggccaaac tgctgggtgc ggaagagaaa gaataccatg   2460
cagaaggagg caaagtgcct atcaagtgga tggcattgga atcaattttta cacagaatct   2520
atacccacca gagtgatgtc tggagctacg gggtgaccgt ttgggagttg atgacctttg   2580
gatccaagcc atatgacgga atccctgcca gcgagatctc ctccatcctg gagaaaggag   2640
aacgcctccc tcagccaccc atatgtacca tcgatgtcta catgatcatg gtcaagtgct   2700
ggatgataga cgcagatagt cgcccaaagt tccgtgagtt gatcatcgaa ttctccaaaa   2760
tggcccgaga ccccagcgc taccttgtca ttcaggggga tgaaagaatg catttgccaa   2820
gtcctacaga ctccaacttc taccgtgccc tgatggatga agaagacatg gacgacgtgg   2880
tggatgccga cgagtacctc atcccacagc agggcttctt cagcagcccc tccacgtcac   2940
ggactcccct cctgagctct ctgagtgcaa ccagcaacaa ttccaccgtg gcttgcattg   3000
atagaaatgg gctgcaaagc tgtcccatca aggaagacag cttcttgcag cgatacagct   3060
cagaccccac aggcgccttg actgaggaca gcatagacga caccttcctc ccagtgcctg   3120
gtgagtggct tgtctggaaa cagtcctgct cctcaacctc ctcgacccac tcagcagcag   3180
ccagtctcca gtgtccaagc caggtgctcc ctccagcatc tccagagggg aaacagtggg   3240
cagatttgca gacacagtga                                              3260

SEQ ID NO: 4           moltype = DNA   length = 3259
FEATURE                Location/Qualifiers
source                 1..3259
                       mol_type = other DNA
                       organism = Homo sapiens
SEQUENCE: 4
atgcgaccct ccgggacggc cggggcagcg ctcctggcgc tgctggctgc gctctgcccg    60
gcgagtcggg ctctggagga aagaaagtt tgccaaggca cgagtaacaa gctcacgcag   120
ttgggcactt ttgaagatca ttttctcagc ctccagagga tgttcaataa ctgtgaggtg   180
gtccttggga atttggaaat tacctatgtg cagaggaatt atgatctttc cttcttaaag   240
accatccagg aggtggctgg ttatgtcctc attgccctca acacagtgga gcgaattcct   300
ttggaaaacc tgcagatcat cagaggaaat atgtactacg aaaattccta tgccttagca   360
gtcttatcta actatgatgc aaataaaacc ggactgaagg agctgcccat gagaaattta   420
cagggacaaa agtgtgatcc aagctgtccc aatgggagct gctggggtgc aggagaggag   480
aactgccaaa aactgaccaa aatcatctgt gcccagcagt gctccgggcg ctgccgtggc   540
aagtcccca gtgactgctg ccacaaccag tgtgctgcag gctgcacagg ccccgggag   600
agcgactgcc tggtctgccg caaattccga gacgaagcca cgtcaagga cacctgcccc   660
ccactcatgc tctacaaccc caccacgtac cagatgtat tgaacccga gggcaaatac   720
agctttggtg ccacctgcgt gaagagtgt cccgtaatt atgtggtgac agatcacggc   780
tcgtcgctcc gagcctgtgg ggccgacagc tatgagatgg aggaagacgg cgtccgcaag   840
tgtaagaagt gcgaaggcc ttgccgcaaa gtgtgtaacg aataggtat tggtgaattt   900
aaagactcac tctccataaa tgctacgaat attaaacact tcaaaaactg cacctccatc   960
agtggcgatc tccacatcct gccggtgca tttaggggtg actccttcac acatactcct  1020
cctctggatc cacaggaact ggatattctg aaaaccgtaa aggaaatcac agggttttg   1080
ctgattcagg cttggcctga aaacaggacg gacctccatg cctttgagaa cctagaaatc  1140
atacgcggca ggaccaagca acatggtcag ttttctcttg cagtcgtcag cctgaacata  1200
acatccttgg gattacgctc cctcaaggag ataagtgatg gagatgtgat aatttcagga  1260
aacaaaaatt tgtgctatgc aaatacaata aactggaaaa actgtttttgg gacctccggt  1320
cagaaaacca aaattataag caacagaggt gaaaacagct gcaaggccac aggccaggtc  1380
tgccatgcct tgtgctcccc cgagggctgc tgggcccgg agcccaggga ctgcgtctct  1440
tgccggaatg tcagccgagg cagggaatgc gtggacaagt gcaaccttct ggagggtgag  1500
ccaagggagt ttgtggagaa ctctgagtgc atacagtgca cccagagtg cctgcctcag  1560
gccatgaaca tcacctgcac aggacgggga ccagacaact gtatccagtg tgcccactac  1620
attgacggcc cccactgcgt caagacctgc ccggcaggag tcatgggaga aacaacacc  1680
ctggtctgga agtacgcaga cgccggccat gtgtgccacc tgtgccatcc aaactgcacc  1740
tacggatgca ctgggccagg tcttgaaggc tgtccaacga atgggcctaa gatcccgtcc  1800
atcgccactg ggatggtggg ggccctcctc ttgctgctgg tggtggccct ggggatcggc  1860
ctcttcatgc gaaggcgcca catcgttcgg aagcgcacgc tgcggaggct gctgcaggag  1920
agggagcttg tggagcctct tacacccagt ggagaagctc caaccaagc tctcttgagg  1980
atcttgaagg aaactgaatt caaaaagatc aaagtgctgg gctccggtgc gttcggcacg  2040
gtgtataagg gactctggat cccagaaggt gagaaagtta aaattccgt cgctatcaag  2100
catctccgaa agccaacaag gaaatcctcg atgagcctac gtgatgggcca gcgtggacaa  2160
ccccacgtg tgccgcctgc tgggcatctg cctcacctcc accgtgcagc tcatcacgca  2220
gctcatgccc ttcggctgcc tcctggacta tgtccgggaa cacaaagaca atattggctc  2280
ccagtacctg gctcaactgg tgtgtcagat cgcaagggtg atgaactact tggaggaccg  2340
tcgcttggtg caccgcgacc tggcagccag gaacgtactg gtgaaaacac cgcagcatgt  2400
caagatcaca gattttgggc tggccaaact gctgggtgcg gaagagaaag aataccatgc  2460
agaaggaggc aaagtgccta tcaagtggat ggcattgaa tcaattttac acagaatcta  2520
tacccaccag agtgatgtct ggagctacgg ggtgaccgtt tgggagttga tgacctttgg  2580
atccaagcca tatgacggaa tccctgccag cgagatctcc tccatcctgg agaaaggaga  2640
acgcctccct cagccaccca tatgtaccat cgatgtctac atgatcatgg tcaagtgctg  2700
gatgatagac gcagatagtc gcccaaagtt ccgtgagttg atcatcgaat tctccaaaat  2760
ggcccgagac cccagcgct accttgtcat tcagggggat gaaagaatgc atttgccaag  2820
tcctacagac tccaacttct accgtgccct gatggatgaa gaagacatgg acgacgtggt  2880
ggatgccgac gagtacctca tcccacagca gggcttcttc agcagcccct ccacgtcacg  2940
gactcccctc ctgagctctc tgagtgcaac cagcaacaat tccaccgtgg cttgcattga  3000
tagaaatggg ctgcaaagct gtcccatcaa ggaagacagc ttcttgcagc gatacagctc  3060
agaccccaca ggcgccttga ctgaggacag catagacgac accttcctcc cagtgcctgg  3120
tgagtggctt gtctggaaac agtcctgctc ctcaacctcc tcgacccact cagcagcagc  3180
cagtctccag tgtccaagcc aggtgctccc tccagcatct ccagagggga aacagtggc  3240
```
agatttgcag acacagtga                                                   3259

SEQ ID NO: 5          moltype = DNA   length = 3276
FEATURE               Location/Qualifiers
source                1..3276
                      mol_type = other DNA
                      organism = Homo sapiens
SEQUENCE: 5
atgcgaccct ccgggacggc cggggcagcg ctcctggcgc tgctggctgc gctctgcccg    60
gcgagtcggg ctctggagga aaagaaagtt tgccaaggca cgagtaacaa gctcacgcag   120
ttgggcactt tgaagatca ttttctcagc ctccagagga tgttcaataa ctgtgaggtg    180
gtccttggga atttggaaat tacctatgtg cagaggaatt atgatctttc cttcttaaag   240
accatccagg aggtggctgg ttatgtcctc attgcccctca acacagtgga gcgaattcct   300
ttggaaaacc tgcagatcat cagaggaaat atgtactacg aaaattccta tgccttagca   360
gtcttatcta actatgatgc aaataaaacc ggactgaagg agctgcccat gagaaattta   420
cagggacaaa agtgtgatcc aagctgtccc aatgggagct gctggggtgc aggagaggag   480
aactgccaga aactgaccaa atcatctgt gcccagcagt gctccgggcg ctgccgtggc   540
aagtcccca gtgactgctg ccacaaccag tgtgctgcag gctgcacagg cccccgggag   600
agcgactgcc tggtctgccg caaattccga gacgaagcca cgtgcaagga cacctgcccc   660
ccactcatgc tctacaaccc caccacgtac cagatggatg tgaacccga gggcaaatac   720
agctttggtg ccacctgcgt gaagaagtgt ccccgtaatt atgtggtgac agatcacggc   780
tcgtgcgtcc gagcctgtgg ggccgacagc tatgagatgg aggaagacgg cgtccgcaag   840
tgtaagaagt gcgaagggcc ttgccgcaaa gtgtgtaacg gaataggtat tggtgaattt   900
aaagactcac tctccataaa tgctacgaat attaaacact tcaaaaactg cacctccatc   960
agtggcgatc tccacatcct gccggtggca tttaggggtg actccttcac acatactcct  1020
cctctggatc cacaggaact ggatattctg aaaaccgtaa ggaaatcaa agggttttg    1080
ctgattcagg cttggcctga aacaggacg gacctccatg cctttgagaa cctagaaatc   1140
atacgcggca ggaccaagca acatggtcag ttttctcttg cagtcgtcag cctgaacata   1200
acatccttgg gattacgctc cctcaaggag ataagtgatg gagatgtgat aatttcagga   1260
aacaaaaatt tgtgctatgc aaatacaata aactggaaaa aactgttgg gacctccggt   1320
cagaaaacca aaattataag caacagaggt gaaacagct gcaaggccac aggccaggtc   1380
tgccatgcct tgtgctcccc cgagggctgc tggggcccgg agcccaggga ctgcgtctct   1440
tgccggaatg tcagccgagg cagggaatgc gtggacaagt gcaacttct ggagggtgag    1500
ccaagggagt ttgtggagaa ctctgagtgc atacagtgcc acccagagtg cctgcctgtg   1560
gccatgaaca tcacctgcac aggacggga ccagacaact gtatccagtg tgcccactac    1620
attgacggcc cccactgcgt caagacctgc ccggcaggag tcatgggaga aaacaacacc   1680
ctggtctgga gtacgcaga cgccggccat gtgtgccacc tgtgccatcc aaactgcacc   1740
tacggatgca ctgggccagg tcttgaaggc tgtccaacga atgggcctaa gatcccgtcc   1800
atcgccactg ggatggtggg ggccctcctc ttgctgctgg tggtgccct ggggatcgtc   1860
ctcttcatgc gaaggcgcca catcgttcgg aagcgcacgc tgcggaggct gctgcaggag   1920
agggagcttg tggagcctct tacacccagt ggagaagctc caaccaagc tctcttgagg    1980
atcttgaagg aaactgaatt caaaaagatc aaagtgctgg gctccggtgc gttcggcacg   2040
gtgtataagg gactctggat cccagaaggt gagaaagtta aaattcccgt cgctatcaag   2100
gaattaagag aagcaacatc tccgaaagcc aacaaggaaa tcctcgatga agcctacgtg   2160
atggccagcg tggacaaccc cacgtgtgcg cctgctggg catctgcct cacctccacc   2220
gtgcagctca tcacgcagct catgcccttc ggctgcctcc tggactatgt ccgggaacac   2280
aaagacaata ttggctccca gtacctgctc aactggtgtg tgcagatcgc aaagggcatg   2340
aactacttgg aggaccgtcg cttggtgcac cgcgacctgg cagccaggaa cgtactggtg   2400
aaaacaccgc agcatgtcaa gatcacagat tttgggctgg ccaaactgct gggtgcggaa   2460
gagaaagaat accatgcaga aggaggcaaa gtgcctatca gtggatggc attggaatca   2520
attttacaca gaatctatac ccaccagagt gatgtctgga gctacggggt gaccgtttgg   2580
gagttgatga ccttttggatc caagccatat gacggaatcc ctgccagcga gatctcctcc   2640
atcctggaga aaggagaacg cctccctcag ccacccatat gtaccatcga tgtctacatg   2700
atcatggtca agtgctggat gatagacgca gatagtcgcc caaagttccg tgagttgatc   2760
atcgaattct ccaaaatggc ccgagacccc cagcgctacc ttgtcattca ggggatgaa   2820
agaatgcatt tgccaagtcc tacagactcc aacttctacc gtgccctgat ggatgaagaa   2880
gacatggacg acgtggtgga tgccgacgag tacctcatcc cacagcaggg cttcttcagc   2940
agcccctcca cgtcacggac tcccctcctg agctctctga gtgcaaccag caacaattcc   3000
accgtggctt gcattgatag aaatgggctc caaagctgtc ccatcaagga agacagcttc   3060
ttgcagcgat acagctcaga ccccacaggc gccttgactg aggacagcat agacgacacc   3120
ttcctcccag tgcctggtga gtggcttgtc tggaaacagt cctgcctctc aacctcctcg   3180
acccactcag cagcagccag tctccagtgt caagccagg tgctccctcc agcatctcca   3240
gagggggaaa cagtggcaga tttgcagaca cagtga                             3276

SEQ ID NO: 6          moltype = AA    length = 93
FEATURE               Location/Qualifiers
source                1..93
                      mol_type = protein
                      organism = Enterobacteria Phage T4
SEQUENCE: 6
MGKSIYQIK NTLNNKVYVG SAKDFEKRWK RHFKDLEKGC HSSIKLQRSF NKHGNVFECS     60
ILEEIPYEKD LIIERENFWI KELNSKINGY NIA                                93

SEQ ID NO: 7          moltype = AA    length = 83
FEATURE               Location/Qualifiers
REGION                1..83
                      note = V117F Mutated Linker
source                1..83
                      mol_type = protein

```
                                    organism = synthetic construct
SEQUENCE: 7
DATFGDTCST HPLKEEIIKK RSETFKAKML KLGPDGRKAL YSKPGSKNGR WNPETHKFCK    60
CGVRIQTSAY TCSKCRNGGS GGS                                           83

SEQ ID NO: 8              moltype = AA   length = 83
FEATURE                   Location/Qualifiers
REGION                    1..83
                          note = V117F K135R N140S Mutated Linker
source                    1..83
                          mol_type = protein
                          organism = synthetic construct
SEQUENCE: 8
DATFGDTCST HPLKEEIIKK RSETVKAKML KLGPDGRKAL YSRPGSKSGR WNPETHKFCK    60
CGVRIQTSAY TCSKCRNGGS GGS                                           83

SEQ ID NO: 9              moltype = AA   length = 83
FEATURE                   Location/Qualifiers
REGION                    1..83
                          note = Linker Domain Variant
source                    1..83
                          mol_type = protein
                          organism = synthetic construct
SEQUENCE: 9
DATFGDTCST HPLKEEIIKK RSETFKAKML KLGPDGRKAL YSRPGSKSGR WNPETHKFCK    60
CGVRIQTSAY TCSKCRNGGS GGS                                           83

SEQ ID NO: 10             moltype = AA   length = 86
FEATURE                   Location/Qualifiers
REGION                    1..86
                          note = Linker Domain Variant
source                    1..86
                          mol_type = protein
                          organism = synthetic construct
SEQUENCE: 10
DATFGDTCST HPLKEEIIKK RSETVKAKML KLGPDGRKAL YSRPGSKSGR WNPETHKFCK    60
CGVRIQTSAY TCSKCRNGGS GGTGGS                                        86

SEQ ID NO: 11             moltype = AA   length = 87
FEATURE                   Location/Qualifiers
REGION                    1..87
                          note = Linker Domain Variant
source                    1..87
                          mol_type = protein
                          organism = synthetic construct
SEQUENCE: 11
DATFGDTCST HPLKEEIIKK RSETVKAKML KLGPDGRKAL YSRPGSKSGR WNPETHKFCK    60
CGVRIQTSAY TCSKCRNGGG GSGGGGS                                       87

SEQ ID NO: 12             moltype = AA   length = 95
FEATURE                   Location/Qualifiers
REGION                    1..95
                          note = Linker Domain Variant
source                    1..95
                          mol_type = protein
                          organism = synthetic construct
SEQUENCE: 12
DATFGDTCST HPLKEEIIKK RSETVKAKML KLGPDGRKAL YSRPGSKSGR WNPETHKFCK    60
CGVRIQTSAY TCSKCRNKES GSVSSEQLAQ FRSLD                              95

SEQ ID NO: 13             moltype = AA   length = 1053
FEATURE                   Location/Qualifiers
source                    1..1053
                          mol_type = protein
                          organism = Staphylococcus aureus
SEQUENCE: 13
MKRNYILGLD IGITSVGYGI IDYETRDVID AGVRLFKEAN VENNEGRRSK RGARRLKRRR    60
RHRIQRVKKL LFDYNLLTDH SELSGINPYE ARVKGLSQKL SEEEFSAALL HLAKRRGVHN   120
VNEVEEDTGN ELSTKEQISR NSKALEEKYV AELQLERLKK DGEVRGSINR FKTSDYVKEA   180
KQLLKVQKAY HQLDQSFIDT YIDLLETRRT YYEGPGEGSP FGWKDIKEWY EMLMGHCTYF   240
PEELRSVKYA YNADLYNALN DLNNLVITRD ENEKLEYYEK FQIIENVFKQ KKKPTLKQIA   300
KEILVNEEDI KGYRVTSTGK PEFTNLKVYH DIKDITARKE IIENAELLDQ IAKILTIYQS   360
SEDIQEELTN LNSELTQEEI EQISNLKGYT GTHNLSLKAI NLILDELWHT NDNQIAIFNR   420
LKLVPKKVDL SQQKEIPTTL VDDFILSPVV KRSFIQSIKV INAIIKKYGL PNDIIIELAR   480
EKNSKDAQKM INEMQKRNRQ TNERIEEIIR TTGKENAKYL IEKIKLHDMQ EGKCLYSLEA   540
IPLEDLLNNP FNYEVDHIIP RSVSFDNSFN NKVLVKQEEN SKKGNRTPFQ YLSSSDSKIS   600
YETFKKHILN LAKGKGRISK TKKEYLLEER DINRFSVQKD FINRNLVDTR YATRGLMNLL   660
RSYFRVNNLD VKVKSINGGF TSFLRRKWKF KKERNKGYKH HAEDALIIAN ADFIFKEWKK   720
LDKAKKVMEN QMFEEKQAES MPEIETEQEY KEIFITPHQI KHIKDFKDYK YSHRVDKKPN   780
```

```
RELINDTLYS TRKDDKGNTL IVNNLNGLYD KDNDKLKKLI NKSPEKLLMY HHDPQTYQKL    840
KLIMEQYGDE KNPLYKYYEE TGNYLTKYSK KDNGPVIKKI KYYGNKLNAH LDITDDYPNS    900
RNKVVKLSLK PYRFDVYLDN GVYKFVTVKN LDVIKKENYY EVNSKCYEEA KKLKKISNQA    960
EFIASFYNND LIKINGELYR VIGVNNDLLN RIEVNMIDIT YREYLENMND KRPPRIIKTI   1020
ASKTQSIKKY STDILGNLYE VKSKKHPQII KKG                                1053

SEQ ID NO: 14           moltype = AA   length = 1053
FEATURE                 Location/Qualifiers
REGION                  1..1053
                        note = SACAS9 D10E Mutant
source                  1..1053
                        mol_type = protein
                        organism = synthetic construct
SEQUENCE: 14
MKRNYILGLE IGITSVGYGI IDYETRDVID AGVRLFKEAN VENNEGRRSK RGARRLKRRR     60
RHRIQRVKKL LFDYNLLTDH SELSGINPYE ARVKGLSQKL SEEEFSAALL HLAKRRGVHN    120
VNEVEEDTGN ELSTKEQISR NSKALEEKYV AELQLERLKK DGEVRGSINR FKTSDYVKEA    180
KQLLKVQKAY HQLDQSFIDT YIDLLETRRT YYEGPGEGSP FGWKDIKEWY EMLMGHCTYF    240
PEELRSVKYA YNADLYNALN DLNNLVITRD ENEKLEYYEK FQIIENVFKQ KKKPTLKQIA    300
KEILVNEEDI KGYRVTSTGK PEFTNLKVYH DIKDITARKE IIENAELLDQ IAKILTIYQS    360
SEDIQEELTN LNSELTQEEI EQISNLKGYT GTHNLSLKAI NLILDELWHT NDNQIAIFNR    420
LKLVPKKVDL SQQKEIPTTL VDDFILSPVV KRSFIQSIKV INAIIKKYGL PNDIIIELAR    480
EKNSKDAQKM INEMQKRNRQ TNERIEEIIR TTGKENAKYL IEKIKLHDMQ EGKCLYSLEA    540
IPLEDLLNNP FNYEVDHIIP RSVSFDNSFN NKVLVKQEEN SKKGNRTPFQ YLSSSDSKIS    600
YETFKKHILN LAKGKGRISK TKKEYLLEER DINRFSVQKD FINRNLVDTR YATRGLMNLL    660
RSYFRVNNLD VKVKSINGGF TSFLRRKWKF KKERNKGYKH HAEDALIIAN ADFIFKEWKK    720
LDKAKKVMEN QMFEEKQAES MPEIETEQEY KEIFITPHQI KHIKDFKDYK YSHRVDKKPN    780
RELINDTLYS TRKDDKGNTL IVNNLNGLYD KDNDKLKKLI NKSPEKLLMY HHDPQTYQKL    840
KLIMEQYGDE KNPLYKYYEE TGNYLTKYSK KDNGPVIKKI KYYGNKLNAH LDITDDYPNS    900
RNKVVKLSLK PYRFDVYLDN GVYKFVTVKN LDVIKKENYY EVNSKCYEEA KKLKKISNQA    960
EFIASFYNND LIKINGELYR VIGVNNDLLN RIEVNMIDIT YREYLENMND KRPPRIIKTI   1020
ASKTQSIKKY STDILGNLYE VKSKKHPQII KKG                                1053

SEQ ID NO: 15           moltype = RNA   length = 21
FEATURE                 Location/Qualifiers
misc_feature            1..21
                        note = Targets CFTR Gene
source                  1..21
                        mol_type = other RNA
                        organism = synthetic construct
SEQUENCE: 15
gcgtcatcaa agcatgccaa c                                              21

SEQ ID NO: 16           moltype = RNA   length = 22
FEATURE                 Location/Qualifiers
misc_feature            1..22
                        note = Targets EGFR Gene
source                  1..22
                        mol_type = other RNA
                        organism = synthetic construct
SEQUENCE: 16
aagccaacaa ggaaatcctc ga                                             22

SEQ ID NO: 17           moltype = AA   length = 1053
FEATURE                 Location/Qualifiers
REGION                  1..1053
                        note = SACAS9 D10E + H557A Mutant
source                  1..1053
                        mol_type = protein
                        organism = synthetic construct
SEQUENCE: 17
MKRNYILGLE IGITSVGYGI IDYETRDVID AGVRLFKEAN VENNEGRRSK RGARRLKRRR     60
RHRIQRVKKL LFDYNLLTDH SELSGINPYE ARVKGLSQKL SEEEFSAALL HLAKRRGVHN    120
VNEVEEDTGN ELSTKEQISR NSKALEEKYV AELQLERLKK DGEVRGSINR FKTSDYVKEA    180
KQLLKVQKAY HQLDQSFIDT YIDLLETRRT YYEGPGEGSP FGWKDIKEWY EMLMGHCTYF    240
PEELRSVKYA YNADLYNALN DLNNLVITRD ENEKLEYYEK FQIIENVFKQ KKKPTLKQIA    300
KEILVNEEDI KGYRVTSTGK PEFTNLKVYH DIKDITARKE IIENAELLDQ IAKILTIYQS    360
SEDIQEELTN LNSELTQEEI EQISNLKGYT GTHNLSLKAI NLILDELWHT NDNQIAIFNR    420
LKLVPKKVDL SQQKEIPTTL VDDFILSPVV KRSFIQSIKV INAIIKKYGL PNDIIIELAR    480
EKNSKDAQKM INEMQKRNRQ TNERIEEIIR TTGKENAKYL IEKIKLHDMQ EGKCLYSLEA    540
IPLEDLLNNP FNYEVDAIIP RSVSFDNSFN NKVLVKQEEN SKKGNRTPFQ YLSSSDSKIS    600
YETFKKHILN LAKGKGRISK TKKEYLLEER DINRFSVQKD FINRNLVDTR YATRGLMNLL    660
RSYFRVNNLD VKVKSINGGF TSFLRRKWKF KKERNKGYKH HAEDALIIAN ADFIFKEWKK    720
LDKAKKVMEN QMFEEKQAES MPEIETEQEY KEIFITPHQI KHIKDFKDYK YSHRVDKKPN    780
RELINDTLYS TRKDDKGNTL IVNNLNGLYD KDNDKLKKLI NKSPEKLLMY HHDPQTYQKL    840
KLIMEQYGDE KNPLYKYYEE TGNYLTKYSK KDNGPVIKKI KYYGNKLNAH LDITDDYPNS    900
RNKVVKLSLK PYRFDVYLDN GVYKFVTVKN LDVIKKENYY EVNSKCYEEA KKLKKISNQA    960
EFIASFYNND LIKINGELYR VIGVNNDLLN RIEVNMIDIT YREYLENMND KRPPRIIKTI   1020
ASKTQSIKKY STDILGNLYE VKSKKHPQII KKG                                1053
```

```
SEQ ID NO: 18              moltype = AA  length = 1053
FEATURE                    Location/Qualifiers
REGION                     1..1053
                           note = SACAS9 D10A + H557A Mutant
source                     1..1053
                           mol_type = protein
                           organism = synthetic construct
SEQUENCE: 18
MKRNYILGLA IGITSVGYGI IDYETRDVID AGVRLFKEAN VENNEGRRSK RGARRLKRRR   60
RHRIQRVKKL LFDYNLLTDH SELSGINPYE ARVKGLSQKL SEEEFSAALL HLAKRRGVHN  120
VNEVEEDTGN ELSTKEQISR NSKALEEKYV AELQLERLKK DGEVRGSINR FKTSDYVKEA  180
KQLLKVQKAY HQLDQSFIDT YIDLLETRRT YYEGPGEGSP FGWKDIKEWY EMLMGHCTYF  240
PEELRSVKYA YNADLYNALN DLNNLVITRD ENEKLEYYEK FQIIENVFKQ KKKPTLKQIA  300
KEILVNEEDI KGYRVTSTGK PEFTNLKVYH DIKDITARKE IIENAELLDQ IAKILTIYQS  360
SEDIQEELTN LNSELTQEEI EQISNLKGYT GTHNLSLKAI NLILDELWHT NDNQIAIFNR  420
LKLVPKKVDL SQQKEIPTTL VDDFILSPVV KRSFIQSIKV INAIIKKYGL PNDIIIELAR  480
EKNSKDAQKM INEMQKRNRQ TNERIEEIIR TTGKENAKYL IEKIKLHDMQ EGKCLYSLEA  540
IPLEDLLNNP FNYEVDAIIP RSVSFDNSFN NKVLVKQEEN SKKGNRTPFQ YLSSSDSKIS  600
YETFKKHILN LAKGKGRISK TKKEYLLEER DINRFSVQKD FINRNLVDTR YATRGLMNLL  660
RSYFRVNNLD VKVKSINGGF TSFLRRKWKF KKERNKGYKH HAEDALIIAN ADFIFKEWKK  720
LDKAKKVMEN QMFEEKQAES MPEIETEQEY KEIFITPHQI KHIKDFKDYK YSHRVDKKPN  780
RELINDTLYS TRKDDKGNTL IVNNLNGLYD KDNDKLKKLI NKSPEKLLMY HHDPQTYQKL  840
KLIMEQYGDE KNPLYKYYEE TGNYLTKYSK KDNGPVIKKI KYYGNKLNAH LDITDDYPNS  900
RNKVVKLSLK PYRFDVYLDN GVYKFVTVKN LDVIKKENYY EVNSKCYEEA KKLKKISNQA  960
EFIASFYNND LIKINGELYR VIGVNNDLLN RIEVNMIDIT YREYLENMND KRPPRIIKTI 1020
ASKTQSIKKY STDILGNLYE VKSKKHPQII KKG                             1053

SEQ ID NO: 19              moltype = AA  length = 1368
FEATURE                    Location/Qualifiers
REGION                     1..1368
                           note = SPCAS9 D10E, D1135E, R1335Q, T1337R Mutant
source                     1..1368
                           mol_type = protein
                           organism = synthetic construct
SEQUENCE: 19
MDKKYSIGLE IGTNSVGWAV ITDEYKVPSK KFKVLGNTDR HSIKKNLIGA LLFDSGETAE   60
ATRLKRTARR RYTRRKNRIC YLQEIFSNEM AKVDDSFFHR LEESFLVEED KKHERHPIFG  120
NIVDEVAYHE KYPTIYHLRK KLVDSTDKAD LRLIYLALAH MIKFRGHFLI EGDLNPDNSD  180
VDKLFIQLVQ TYNQLFEENP INASGVDAKA ILSARLSKSR RLENLIAQLP GEKKNGLFGN  240
LIALSLGLTP NFKSNFDLAE DAKLQLSKDT YDDDLDNLLA QIGDQYADLF LAAKNLSDAI  300
LLSDILRVNT EITKAPLSAS MIKRYDEHHQ DLTLLKALVR QQLPEKYKEI FFDQSKNGYA  360
GYIDGGASQE EFYKFIKPIL EKMDGTEELL VKLNREDLLR KQRTFDNGSI PHQIHLGELH  420
AILRRQEDFY PFLKDNREKI EKILTFRIPY YVGPLARGNS RFAWMTRKSE ETITPWNFEE  480
VVDKGASAQS FIERMTNFDK NLPNEKVLPK HSLLYEYFTV YNELTKVKYV TEGMRKPAFL  540
SGEQKKAIVD LLFKTNRKVT VKQLKEDYFK KIECFDSVEI SGVEDRFNAS LGTYHDLLKI  600
IKDKDFLDNE ENEDILEDIV LTLTLFEDRE MIEERLKTYA HLFDDKVMKQ LKRRRYTGWG  660
RLSRKLINGI RDKQSGKTIL DFLKSDGFAN RNFMQLIHDD SLTFKEDIQK AQVSGQGDSL  720
HEHIANLAGS PAIKKGILQT VKVVDELVKV MGRHKPENIV IEMARENQTT QKGQKNSRER  780
MKRIEEGIKE LGSQILKEHP VENTQLQNEK LYLYYLQNGR DMYVDQELDI NRLSDYDVDH  840
IVPQSFLKDD SIDNKVLTRS DKNRGKSDNV PSEEVVKKMK NYWRQLLNAK LITQRKFDNL  900
TKAERGGLSE LDKAGFIKRQ LVETRQITKH VAQILDSRMN TKYDENDKLI REVKVITLKS  960
KLVSDFRKDF QFYKVREINN YHHAHDAYLN AVVGTALIKK YPKLESEFVY GDYKVYDVRK 1020
MIAKSEQEIG KATAKYFFYS NIMNFFKTEI TLANGEIRKR PLIETNGETG EIVWDKGRDF 1080
ATVRKVLSMP QVNIVKKTEV QTGGFSKESI LPKRNSDKLI ARKKDWDPKK YGGFESPTVA 1140
YSVLVVAKVE KGKSKKLKSV KELLGITIME RSSFEKNPID FLEAKGYKEV KKDLIIKLPK 1200
YSLFELENGR KRMLASAGEL QKGNELALPS KYVNFLYLAS HYEKLKGSPE DNEQKQLFVE 1260
QHKHYLDEII EQISEFSKRV ILADANLDKV LSAYNKHRDK PIREQAENII HLFTLTNLGA 1320
PAAFKYFDTT IDRKQYRSTK EVLDATLIHQ SITGLYETRI DLSQLGGD                1368

SEQ ID NO: 20              moltype = AA  length = 1368
FEATURE                    Location/Qualifiers
REGION                     1..1368
                           note = SPCAS9 D10E, H840A, D1135E, R1335Q, T1337R Mutant
source                     1..1368
                           mol_type = protein
                           organism = synthetic construct
SEQUENCE: 20
MDKKYSIGLE IGTNSVGWAV ITDEYKVPSK KFKVLGNTDR HSIKKNLIGA LLFDSGETAE   60
ATRLKRTARR RYTRRKNRIC YLQEIFSNEM AKVDDSFFHR LEESFLVEED KKHERHPIFG  120
NIVDEVAYHE KYPTIYHLRK KLVDSTDKAD LRLIYLALAH MIKFRGHFLI EGDLNPDNSD  180
VDKLFIQLVQ TYNQLFEENP INASGVDAKA ILSARLSKSR RLENLIAQLP GEKKNGLFGN  240
LIALSLGLTP NFKSNFDLAE DAKLQLSKDT YDDDLDNLLA QIGDQYADLF LAAKNLSDAI  300
LLSDILRVNT EITKAPLSAS MIKRYDEHHQ DLTLLKALVR QQLPEKYKEI FFDQSKNGYA  360
GYIDGGASQE EFYKFIKPIL EKMDGTEELL VKLNREDLLR KQRTFDNGSI PHQIHLGELH  420
AILRRQEDFY PFLKDNREKI EKILTFRIPY YVGPLARGNS RFAWMTRKSE ETITPWNFEE  480
VVDKGASAQS FIERMTNFDK NLPNEKVLPK HSLLYEYFTV YNELTKVKYV TEGMRKPAFL  540
SGEQKKAIVD LLFKTNRKVT VKQLKEDYFK KIECFDSVEI SGVEDRFNAS LGTYHDLLKI  600
IKDKDFLDNE ENEDILEDIV LTLTLFEDRE MIEERLKTYA HLFDDKVMKQ LKRRRYTGWG  660
```

```
RLSRKLINGI RDKQSGKTIL DFLKSDGFAN RNFMQLIHDD SLTFKEDIQK AQVSGQGDSL  720
HEHIANLAGS PAIKKGILQT VKVVDELVKV MGRHKPENIV IEMARENQTT QKGQKNSRER  780
MKRIEEGIKE LGSQILKEHP VENTQLQNEK LYLYYLQNGR DMYVDQELDI NRLSDYDVDA  840
IVPQSFLKDD SIDNKVLTRS DKNRGKSDNV PSEEVVKKMK NYWRQLLNAK LITQRKFDNL  900
TKAERGGLSE LDKAGFIKRQ LVETRQITKH VAQILDSRMN TKYDENDKLI REVKVITLKS  960
KLVSDFRKDF QFYKVREINN YHHAHDAYLN AVVGTALIKK YPKLESEFVY GDYKVYDVRK 1020
MIAKSEQEIG KATAKYFFYS NIMNFFKTEI TLANGEIRKR PLIETNGETG EIVWDKGRDF 1080
ATVRKVLSMP QVNIVKKTEV QTGGFSKESI LPKRNSDKLI ARKKDWDPKK YGGFESPTVA 1140
YSVLVVAKVE KGKSKKLKSV KELLGITIME RSSFEKNPID FLEAKGYKEV KKDLIIKLPK 1200
YSLFELENGR KRMLASAGEL QKGNELALPS KYVNFLYLAS HYEKLKGSPE DNEQKQLFVE 1260
QHKHYLDEII EQISEFSKRV ILADANLDKV LSAYNKHRDK PIREQAENII HLFTLTNLGA 1320
PAAFKYFDTT IDRKQYRSTK EVLDATLIHQ SITGLYETRI DLSQLGGD            1368
```